United States Patent
Godden et al.

(10) Patent No.: US 11,416,472 B2
(45) Date of Patent: Aug. 16, 2022

(54) AUTOMATED COMPUTING PLATFORM FOR AGGREGATING DATA FROM A PLURALITY OF INCONSISTENTLY CONFIGURED DATA SOURCES TO ENABLE GENERATION OF REPORTING RECOMMENDATIONS

(71) Applicant: UnitedHealth Group Incorporated, Minnetonka, MN (US)

(72) Inventors: Paul J. Godden, London (GB); Gregory J. Boss, Saginaw, MI (US); Sarah McCandless, Raleigh, NC (US); Art Swanson, Cary, NC (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 354 days.

(21) Appl. No.: 16/597,489

(22) Filed: Oct. 9, 2019

(65) Prior Publication Data

US 2021/0109915 A1    Apr. 15, 2021

(51) Int. Cl.
*G06F 7/00* (2006.01)
*G06F 16/23* (2019.01)
(Continued)

(52) U.S. Cl.
CPC ............ *G06F 16/2365* (2019.01); *G06F 9/54* (2013.01); *G06F 15/00* (2013.01); *G06F 16/258* (2019.01);
(Continued)

(58) Field of Classification Search
CPC ...... G06F 16/2365; G06F 16/258; G06F 9/54; G06F 15/00; G16H 10/60; G16H 15/00; G06N 20/00; G06N 5/04
(Continued)

(56) References Cited

U.S. PATENT DOCUMENTS 7,702,605 B2    4/2010  Friedlander et al.
7,752,154 B2    7/2010  Frielander et al.
(Continued)

FOREIGN PATENT DOCUMENTS

AU    2015213399 A1    3/2016
AU    2017210493 A1    8/2017
(Continued)

OTHER PUBLICATIONS

"HUGO Gene Nomenclature Committee—The Resource For Approved Human Gene Nomenclature," (online), [Retrieved from the Internet Oct. 15, 2021] <URL: https://www.genenames.org/>.
(Continued)

*Primary Examiner* — Isaac M Woo
(74) *Attorney, Agent, or Firm* — Alston & Bird LLP

(57) ABSTRACT

Methods, apparatus, systems, computing devices, computing entities, and/or the like for generating medical research reports automatically collect data from a plurality of separate health data storage systems, standardize the received data to support at least a requested report type, apply one or more machine-learning quality control check to identify potentially inaccurate data included within the received data, and to generate the requested report based at least in part on the standardized, refined data. Moreover, one or more recommended additional reports supported by the refined data set is identified and recommended to a user based at least in part on user attributes and reports initially requested.

18 Claims, 11 Drawing Sheets

(51) Int. Cl.
*G06F 15/00* (2006.01)
*G06F 9/54* (2006.01)
*G16H 10/60* (2018.01)
*G06N 20/00* (2019.01)
*G06N 5/04* (2006.01)
*G16H 15/00* (2018.01)
*G06F 16/25* (2019.01)

(52) U.S. Cl.
CPC .............. *G06N 5/04* (2013.01); *G06N 20/00* (2019.01); *G16H 10/60* (2018.01); *G16H 15/00* (2018.01)

(58) Field of Classification Search
USPC .................................................. 707/600–899
See application file for complete search history.

(56) References Cited

U.S. PATENT DOCUMENTS

| | | |
|---|---|---|
| 7,788,203 B2 | 8/2010 | Friedlander et al. |
| 7,792,776 B2 | 9/2010 | Friedlander et al. |
| 7,805,391 B2 | 9/2010 | Friedlander et al. |
| 7,809,660 B2 | 10/2010 | Friedlander et al. |
| 7,853,611 B2 | 12/2010 | Friedlander et al. |
| 7,917,478 B2 | 3/2011 | Friedlander et al. |
| 8,055,603 B2 | 11/2011 | Angell et al. |
| 8,135,740 B2 | 3/2012 | Friedlander et al. |
| 8,145,582 B2 | 3/2012 | Angell et al. |
| 8,731,966 B2 | 5/2014 | Breitenstein et al. |
| 10,886,013 B1 * | 1/2021 | Matthews ............. G06N 20/00 |
| 2008/0082356 A1 | 4/2008 | Friedlander et al. |
| 2008/0208813 A1 | 8/2008 | Friedlander et al. |
| 2008/0208814 A1 | 8/2008 | Friedlander et al. |
| 2008/0208838 A1 | 8/2008 | Friedlander et al. |
| 2008/0208875 A1 | 8/2008 | Friedlander et al. |
| 2008/0208901 A1 | 8/2008 | Friedlander et al. |
| 2008/0278334 A1 | 11/2008 | Friedlander et al. |
| 2008/0288430 A1 | 11/2008 | Friedlander et al. |
| 2008/0294459 A1 | 11/2008 | Angell et al. |
| 2008/0294692 A1 | 11/2008 | Angell et al. |
| 2009/0024414 A1 | 1/2009 | Mansour et al. |
| 2009/0024553 A1 | 1/2009 | Angell et al. |
| 2009/0287503 A1 | 11/2009 | Angell et al. |
| 2011/0071674 A1 | 3/2011 | Friedlander et al. |
| 2011/0077958 A1 | 3/2011 | Breitenstein et al. |
| 2011/0077972 A1 | 3/2011 | Breitenstein et al. |
| 2011/0077973 A1 | 3/2011 | Breitenstein et al. |
| 2012/0035963 A1 | 2/2012 | Qian et al. |
| 2013/0339060 A1 | 12/2013 | Delaney et al. |
| 2014/0324472 A1 | 10/2014 | Delaney et al. |
| 2016/0048655 A1 | 2/2016 | Maitra et al. |
| 2016/0092641 A1 | 3/2016 | Delaney et al. |
| 2016/0203269 A1 | 7/2016 | Breitenstein et al. |
| 2016/0314249 A1 | 10/2016 | Dunleavy |
| 2018/0018432 A1 | 1/2018 | Dunleavy |
| 2018/0096105 A1 | 4/2018 | Bleicher et al. |

FOREIGN PATENT DOCUMENTS

| | | |
|---|---|---|
| CA | 2693995 A1 | 1/2009 |
| CA | 2827454 A1 | 8/2012 |
| CN | 102365641 A | 2/2012 |
| CO | 6930061 A1 | 4/2014 |
| EP | 2985711 A1 | 2/2016 |
| EP | 3327727 A2 | 11/2017 |
| GB | 2463593 A | 3/2010 |
| GB | 2559022 A | 7/2018 |
| JP | 2018-514862 A | 6/2018 |
| WO | 2009/011736 A1 | 1/2009 |
| WO | 2010/109351 A1 | 9/2010 |
| WO | 2012/112761 A2 | 8/2012 |
| WO | 2015/155588 A2 | 10/2015 |
| WO | 2017/106851 A1 | 6/2017 |

OTHER PUBLICATIONS

Carroll, Nikki et al. "PS1-05: Feasibility of Extracting Oncology Treatment Data from on Electronic Health Record," Clinical Medicine & Research, vol. 9, Nos. 3-4, p. 169, Nov. 2011, DOI: 10.3121/cmr.2011.1020.ps1-05, PMCID: PMC3251467.

Kent, Jessica. "Clinical Decision Support from Dana-Farber Powers Cancer Care," Health IT Analytics, Jun. 22, 2018, (5 pages), (article, online), [Retrieved from the Internet Oct. 15, 2021] <URL: https://healthitanalytics.com/news/clinical-decision-support-from-dana-farber-powers-cancer-care>.

Li, Jenny Jing et al. "Effective Use Of Electronic Medical Record (EMR) Data In Analysis Of Association Between KRAS Mutations and Depression In Colorectal Cancer Patients," Journal of Clinical Oncology, vol. 36, No. 4_suppl, Feb. 1, 2018, published online Feb. 26, 2018, (4 pages), (article, online), DOI: 10.1200/JCO.2018.36.4_suppl.861.

Manion, Frank J. et al. "Leveraging EHR Data For Outcomes and Comparative Effectiveness Research In Oncology," Author Manuscript, Current Oncology Reports, vol. 14, No. 6, Dec. 2012, (11 pages), DOI: 10.1007/s11912-012-0272-6, PMCID: PMC3490017, NIHMSID: NIHMS406491, PMID: 22948276.

Seneviratne, Martin G. et al. "Architecture and Implementation Of A Clinical Research Data Warehouse For Prostate Cancer," eGEMs (Generating Evidence & Methods To Improve Patient Outcomes) The Journal for Electronic Health Data and Methods, vol. 1, No. 1:13, pp. 1-7, DOI: https://doi.org/10.5334/egems.234.

Walsh, Sean et al. "Decision Support Systems In Oncology," JCO Clinical Cancer Informatics, vol. 3, (18 pages), Feb. 7, 2019, (article, online), DOI: 10.1200/CCI.18.00001, PMID: 30730766.

Weiskopf, Nicole G. et al. "A Data Quality Assessment Guideline for Electronic Health Record Data Reuse," eGEMs (Generating Evidence & Methods To Improve Patient Outcomes), The Journal for Electronic Health Data and Methods, Sep. 4, 2017, vol. 5, No. 1:14, pp. 1-19, DOI: 10.5334/egems.218, PMCID: PMC5983018, PMID: 29881734.

\* cited by examiner

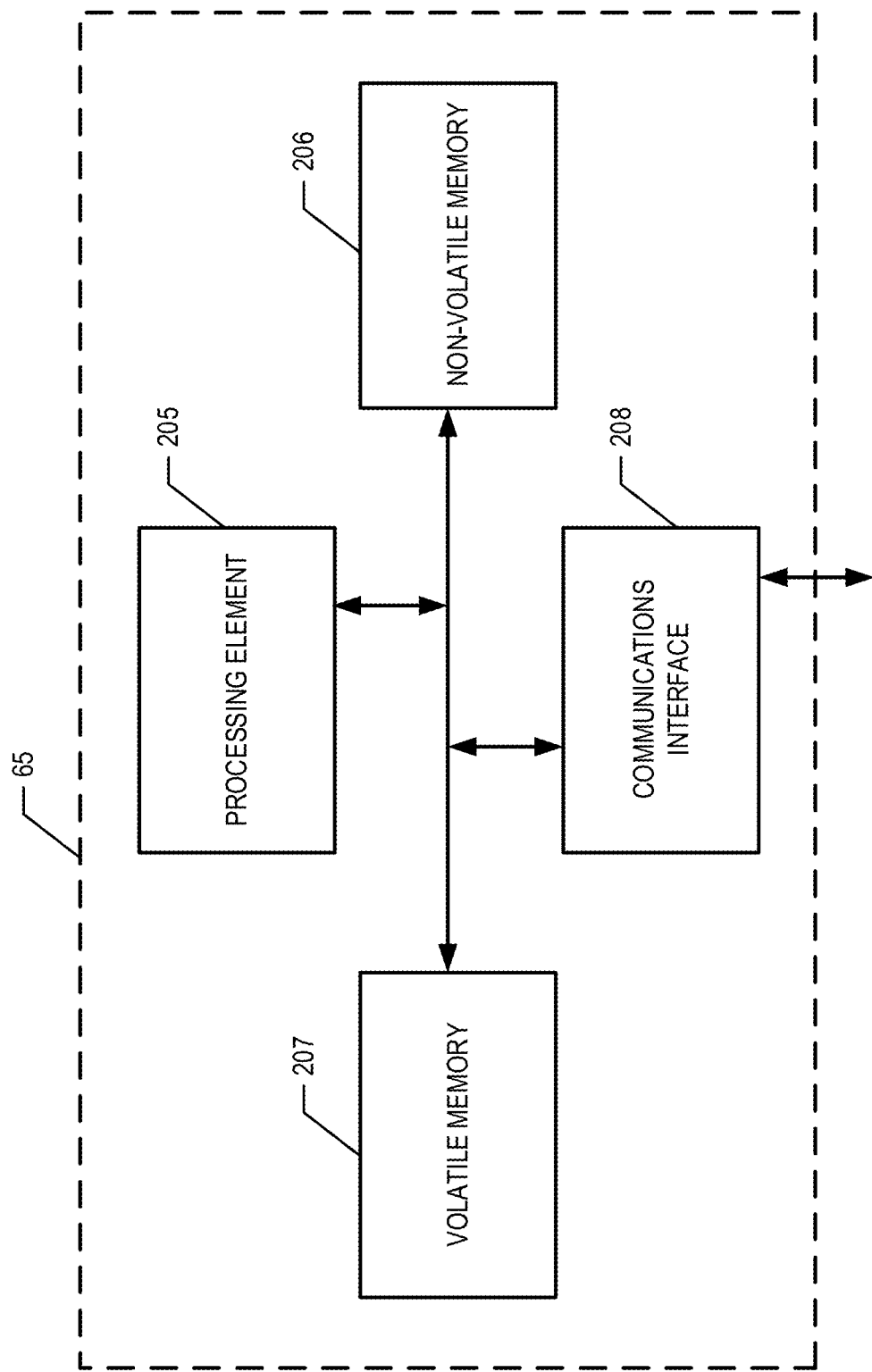

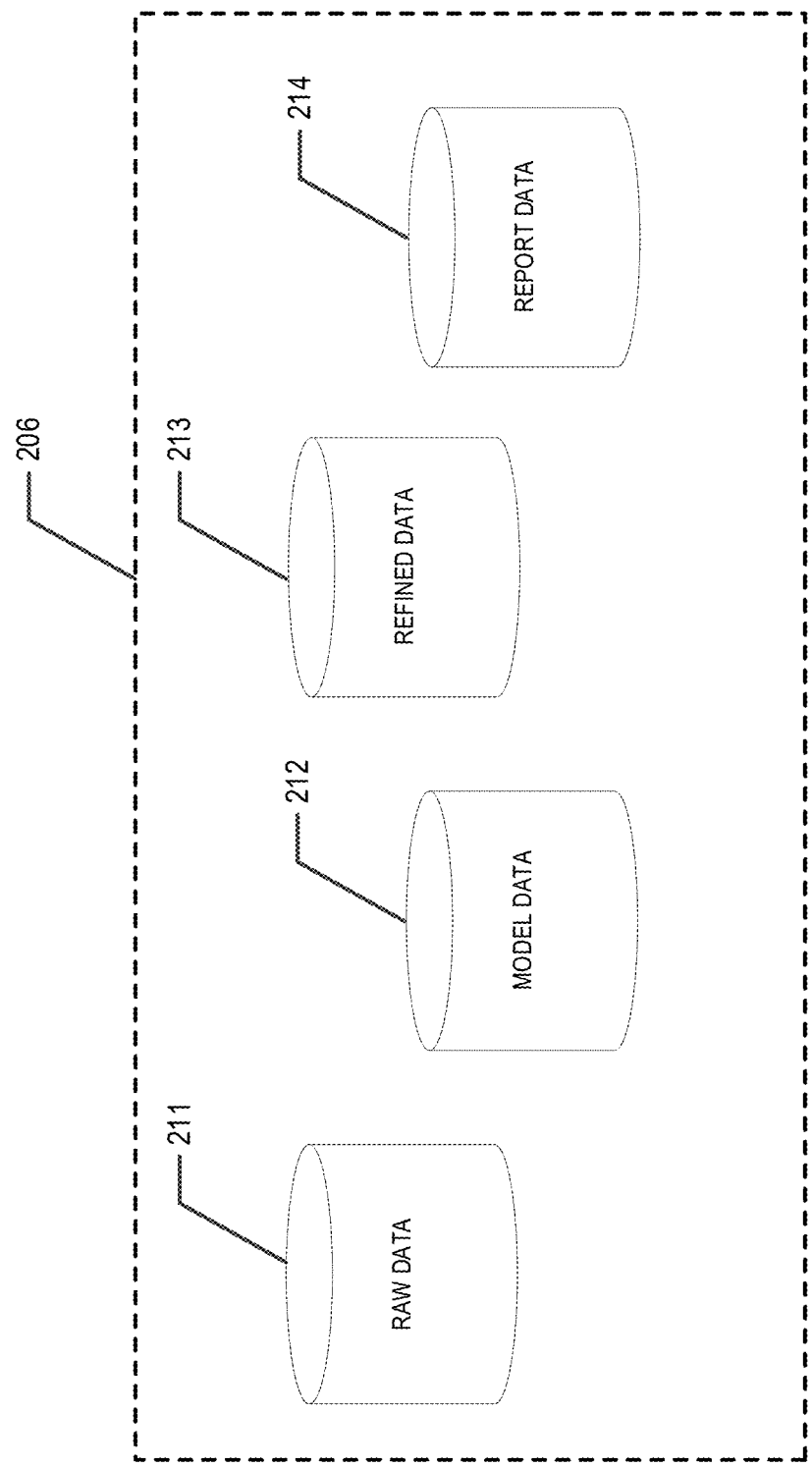

AUTOMATED COMPUTING PLATFORM FOR AGGREGATING DATA FROM A PLURALITY OF INCONSISTENTLY CONFIGURED DATA SOURCES TO ENABLE GENERATION OF REPORTING RECOMMENDATIONS

TECHNOLOGICAL FIELD

Embodiments of the present invention generally relate to systems and methods for aggregating and standardizing retrospective clinical data from a plurality of electronic health-related data sources, such as electronic medical record (EMR) data sources and for automatically producing research reports determined to be relevant for a particular user based on machine-learning.

BACKGROUND

Medical studies are generally performed using data collected according to one of two potential data collection methodologies. The most easily recognizable data collection method is through one or more experiments and/or observational periods designed prospectively, to collect data from one or more designated subjects in accordance with well-defined data collection techniques which are often specified by the corresponding study for which the data is collected. Other medical studies utilize retrospective data, which generally (though not exclusively) encompasses clinical data generated by a healthcare provider when caring for a particular patient. The data is thus generated and/or collected primarily for the purpose of helping with the patient's healthcare, rather than collecting data for experimental and/or research purposes. Although common in several fields of medicine, these retrospective data analyses are particularly relevant in the field of oncology, as new hypotheses for treating cancer often arise much more quickly than longitudinal patient studies can be funded, assembled, and carried out.

Due to the very nature of clinically-generated data as being generated as patient-centric data, clinical data is often highly variable in terms of content, quality, and detail. Even among clinical data generated by/for a single physician, clinical data can vary widely as the physician tailors his/her treatment to the particular patient. Thus, when utilizing clinical data for a retrospective data analysis, researchers generally must spend a great deal of resources to standardize the clinical data to identify trends within the retrospective clinical data and/or to generate usable, substantive comparisons between the clinical data.

Accordingly, a need exists for systems and methods for automatic standardization of clinical data and for automatic generation of relevant data analysis.

BRIEF SUMMARY

In general, embodiments of the present invention provide methods, apparatus, systems, computing devices, computing entities, and/or the like. In accordance with one embodiment, a computer-implemented method for automatically standardizing data received from a plurality of electronic health data sources to generate one or more graphical reports is provided. In various embodiments, the method comprises: receiving, by one or more processors, report initiation data identifying one or more requested reports; receiving, via a plurality of data transmission interfaces, raw health data from a plurality of health data storage systems, wherein the raw health data from each of the plurality of health data storage systems is received through corresponding data transmission interfaces collectively configured to standardize the raw health data into a single data set; applying, via the one or more processors, a machine-learning quality control check to identify inaccurate data included within the raw health data; upon identifying inaccurate data within the raw health data, remediating, via the one or more processors, the inaccurate data within the raw health data; after remediating the inaccurate data within the raw health data, generating, via the one or more processors, a refined data table comprising standardized report data relevant for the one or more requested reports, wherein the standardized report data is generated from the raw health data received from the plurality of health data storage systems; and generating one or more of the requested reports based at least in part on the refined data table.

In certain embodiments, the method further comprises: receiving, user profile data corresponding to a user; determining, via a machine-learning algorithm, one or more additional reports supported by the refined data table; determining a relevance score for each of the one or more additional reports based at least in part on user attribute data reflected within the user profile data; determining one or more recommended additional reports selected from the one or more additional reports based at least in part on the relevance score generated for each of the one or more additional reports; generating a graphical display identifying the one or more recommended additional reports for the user.

In various embodiments, the method further comprises: querying a report database based at least in part on the report initiation data identifying one or more requested reports to determine standardized report data utilized to generate the one or more requested reports; and wherein generating the refined data table comprises generating table entries corresponding to the determined standardized report data utilized to generate the one or more requested reports within the refined data table. Moreover, in certain embodiments, receiving raw health data from a plurality of health data storage systems further comprises standardizing the raw health data via Application Program Interfaces (APIs) executed by the corresponding data transmission interfaces.

In various embodiments, generating the one or more requested reports comprises: determining an intended use for each of the one or more requested reports; querying a formatting database based at least in part on the intended use determined for each of the one or more requested reports to determine formatting data relevant for each of the one or more requested reports; and generating the one or more requested reports based at least in part on formatting data relevant for each of the one or more requested reports. In certain embodiments, receiving raw health data from a plurality of health data storage systems further comprises: scanning each of the one or more health data storage systems to determine data formats corresponding to raw health data received from each of the one or more health data storage systems; and assigning a data transmission interface to each of the one or more health data storage systems based at least in part on the data formats determined to corresponding to raw data received from each of the one or more health data storage systems.

In various embodiments, generating a refined data table further comprises automatically assigning a standard procedure code for data entries within the standardized report data.

In accordance with another aspect, a computing system comprising a non-transitory computer readable storage medium and one or more processors is provided. In certain embodiments, the computing system configured to: receive report initiation data identifying one or more requested reports; receive via a plurality of data transmission interfaces, raw health data from a plurality of health data storage systems, wherein the raw health data from each of the plurality of health data storage systems is received through corresponding data transmission interfaces configured to standardize the raw health data; apply a machine-learning quality control check to identify inaccurate data included within the raw health data; upon identifying inaccurate data within the raw health data, remediate the inaccurate data within the raw health data; after remediating the inaccurate data within the raw health data, generate a refined data table comprising standardized report data relevant for the one or more requested reports, wherein the standardized report data is generated from the raw health data received from the plurality of health data storage systems; and generate the one or more requested reports based at least in part on the refined data table.

In various embodiments, the computing system is further configured to: receive user profile data corresponding to a user; determine, via a machine-learning algorithm, one or more additional reports supported by the refined data table; determine a relevance score for each of the one or more additional reports based at least in part on user attribute data reflected within the user profile data; determine one or more recommended additional reports selected from the one or more additional reports based at least in part on the relevance score generated for each of the one or more additional reports; generate a graphical display identifying the one or more recommended additional reports for the user.

In certain embodiments, the computing system is further configured to: query a report database based at least in part on the report initiation data identifying one or more requested reports to determine standardized report data utilized to generate the one or more requested reports; and wherein generating the refined data table comprises generating table entries corresponding to the determined standardized report data utilized to generate the one or more requested reports within the refined data table. Moreover, receiving raw health data from a plurality of health data storage systems may further comprise standardizing the raw health data via Application Program Interfaces (APIs) executed by the corresponding data transmission interfaces. In certain embodiments, generating the one or more requested reports comprises: determining an intended use for each of the one or more requested reports; querying a formatting database based at least in part on the intended use determined for each of the one or more requested reports to determine formatting data relevant for each of the one or more requested reports; and generating the one or more requested reports based at least in part on formatting data relevant for each of the one or more requested reports.

In various embodiments, receiving raw health data from a plurality of health data storage systems further comprises: scanning each of the one or more health data storage systems to determine data formats corresponding to raw health data received from each of the one or more health data storage systems; and assigning a data transmission interface to each of the one or more health data storage systems based at least in part on the data formats determined to corresponding to raw data received from each of the one or more health data storage systems.

In certain embodiments, generating a refined data table further comprises automatically assigning a standard procedure code for data entries within the standardized report data.

Various embodiments are directed to a computer program product comprising a non-transitory computer readable medium having computer program instructions stored therein, the computer program instructions when executed by a processor, cause the processor to: receive report initiation data identifying one or more requested reports; receive via a plurality of data transmission interfaces, raw health data from a plurality of health data storage systems, wherein the raw EMR data from each of the plurality of health data storage systems is received through corresponding data transmission interfaces configured to standardize the raw health data; apply a machine-learning quality control check to identify inaccurate data included within the raw health data; upon identifying inaccurate data within the raw health data, remediate the inaccurate data within the raw health data; after remediating the inaccurate data within the raw health data, generate a refined data table comprising standardized report data relevant for the one or more requested reports, wherein the standardized report data is generated from the raw health data received from the plurality of health data storage systems; and generate the one or more requested reports based at least in part on the refined data table.

In certain embodiments, the computer program instructions are further configured to, when executed by a processor, cause the processor to: receive user profile data corresponding to a user; determine, via a machine-learning algorithm, one or more additional reports supported by the refined data table; determine a relevance score for each of the one or more additional reports based at least in part on user attribute data reflected within the user profile data; determine one or more recommended additional reports selected from the one or more additional reports based at least in part on the relevance score generated for each of the one or more additional reports; generate a graphical display identifying the one or more recommended additional reports for the user.

In various embodiments, the computer program instructions are further configured to, when executed by a processor, cause the processor to: query a report database based at least in part on the report initiation data identifying one or more requested reports to determine standardized report data utilized to generate the one or more requested reports; and wherein generating the refined data table comprises generating table entries corresponding to the determined standardized report data utilized to generate the one or more requested reports within the refined data table.

In certain embodiments, receiving raw health data from a plurality of health data storage systems further comprises standardizing the raw health data via Application Program Interfaces (APIs) executed by the corresponding data transmission interfaces. Moreover, generating the one or more requested reports may comprise: determining an intended use for each of the one or more requested reports; querying a formatting database based at least in part on the intended use determined for each of the one or more requested reports to determine formatting data relevant for each of the one or more requested reports; and generating the one or more requested reports based at least in part on formatting data relevant for each of the one or more requested reports.

In certain embodiments, receiving raw health data from a plurality of health data storage systems further comprises: scanning each of the one or more health data storage systems to determine data formats corresponding to raw health data received from each of the one or more health data storage systems; and assigning a data transmission interface to each of the one or more health data storage systems based at least in part on the data formats determined to corresponding to raw data received from each of the one or more health data storage systems. Moreover, generating a refined data table further comprises automatically assigning a standard procedure code for data entries within the standardized report data.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 2A is a schematic of an analytic computing entity in accordance with certain embodiments of the present invention;

FIG. 2B is a schematic representation of a memory media storing a plurality of repositories, databases, data stores, and/or relational tables;

DETAILED DESCRIPTION OF SOME EXAMPLE EMBODIMENTS

Figure 1:
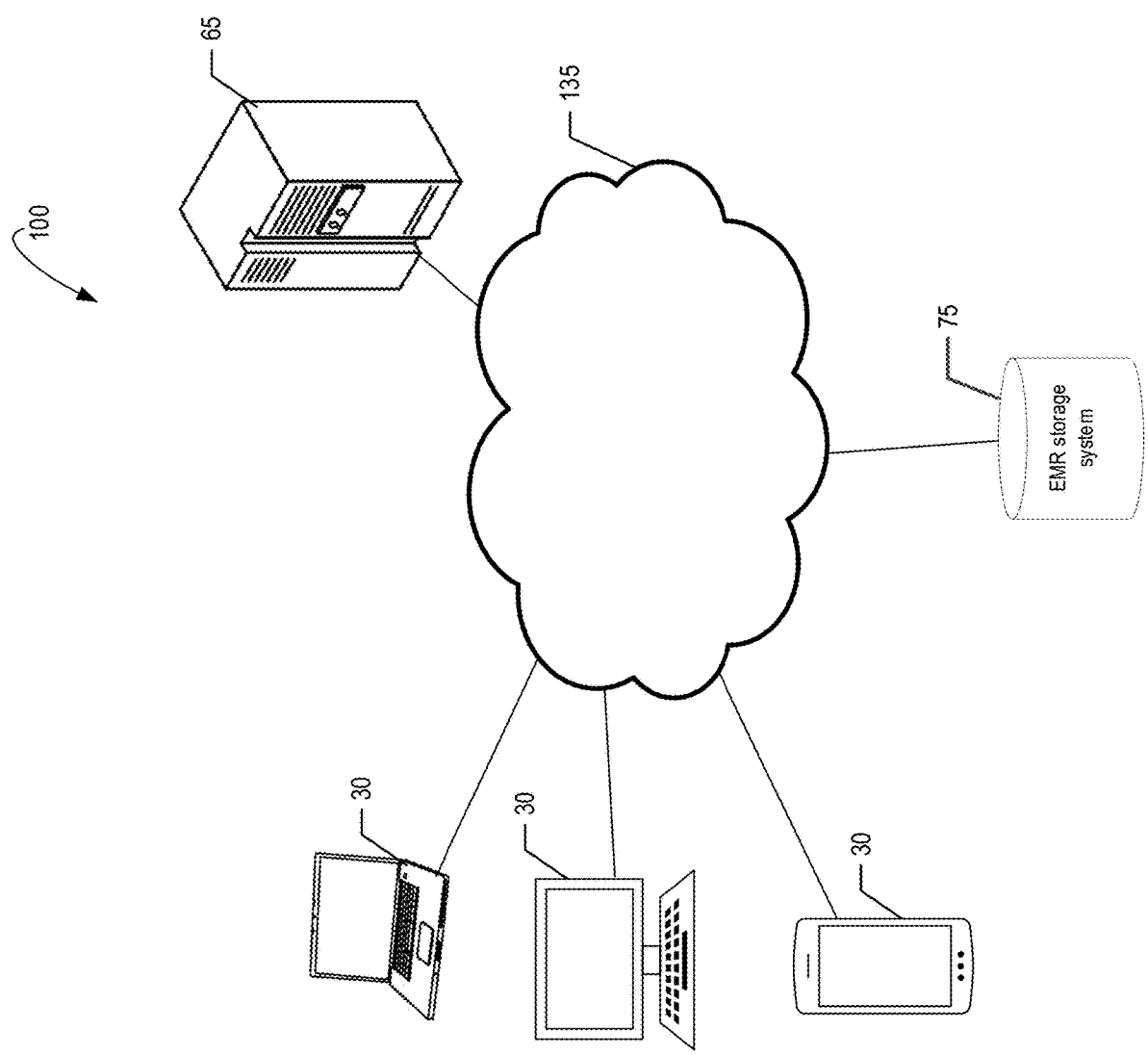
FIG. 1 is a diagram of a pre-approval system that can be used in conjunction with various embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a research system 100 that can be used in conjunction with various embodiments of the present invention. As shown in FIG. 1, the research system 100 may comprise one or more analytic computing entities 65, one or more user computing entities 30 (e.g., a user computing entity 30 associated with a provider usable to provide data to the analytic computing entity 65; and/or the like), one or more health data storage systems 75 (such as EMR storage systems, clinical data storage systems (e.g., Patient Access Solutions (PAS) systems, Radiology Information Systems (RIS), patient-reported outcome storage systems, public-domain genomics resources, and/or the like) or other data sources as discussed herein), one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrates certain system entities as separate, standalone entities, the various embodiments are not limited to this particular architecture.

a. Exemplary Analytic Computing Entity

FIG. 2A provides a schematic of an analytic computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

Although illustrated as a single computing entity, it should be understood that the analytic computing entity 65 may be embodied as a plurality of computing entities, tools, and/or the like operating collectively to perform one or more processes, methods, and/or steps. As just one non-limiting example, the analytic computing entity 65 may comprise a plurality of individual data tools, such as an extraction tool 651, a quality control tool 652, a reporting tool 653, and/or the like. Each of these tools may perform specified tasks and/or processes, such that collectively, the analytic computing entity 65 may be configured to execute one or more tasks requested by a user.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with other computing entities, one or more user computing entities 30, and/or the like. In certain embodiments, the analytic computing entity 65 may be configured to receive data from one or more data sources (e.g., to be utilized for generating one or more reports), and the analytic computing entity 65 may be configured to receive data indicative of user input, for example, from a user computing entity 30, which may be usable for identifying reporting types requested, for generating training data for one or more machine-learning algorithms (e.g., based on user input classifying particular data records as erroneous, not erroneous, relevant, irrelevant, and/or the like).

As shown in FIG. 2A, in one embodiment, the analytic computing entity 65 may include or be in communication with one or more processing elements 205 (also referred to as processors, processing circuitry, and/or similar terms used herein interchangeably) that communicate with other elements within the analytic computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the analytic computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the oncological research system may be stored. As a person of ordinary skill in the art would recognize, the information/data required for the operation of the oncological research system may also be partially stored in the cloud data storage system and partially stored in a locally maintained data storage system.

Memory media 206 may include information/data accessed and stored by the research system to facilitate the operations of the system. More specifically, memory media 206 may encompass one or more data stores configured to store information/data usable in certain embodiments. For example, as shown in FIG. 2B, data stores encompassed within the memory media 206 may comprise a raw data store 211, a model data store 212, a refined data store 213, a report data store 214, and/or the like.

As illustrated in FIG. 2B, the data stores 206 may comprise raw information/data 211 received directly from one or more data sources for storage therein prior to consolidating and refining the same. The term raw data is used generally to refer to any data that has been received from a data source but which has not yet been analyzed for quality control and/or refinement Continuing with FIG. 2B, the data stores 206 may comprise model data 212. The model data 212 may comprise data indicative of machine learning algorithms utilized to achieve various data refinement and/or analysis as discussed herein, as well as any training data that may be utilized for training those machine learning algorithms.

Continuing with FIG. 2B, the data stores 206 may comprise refined information/data reflecting one or more data tables produced as a result of data consolidation (from multiple data sources), quality control procedures, and/or data refinement procedures as discussed herein. Data stored within the refined data store is utilized for generation of one or more reports.

Finally, as shown in FIG. 2B, the data stores 206 may comprise report data, which may be indicative of types of reports available for generation by the analytic computing entity 65. In other embodiments, generated final reports may additionally be stored within the report data storage area, for later access and retrieval by users.

In one embodiment, the analytic computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 308. Thus, the databases, database instances, database management system entities, data, applications, programs, program modules, scripts, source code, object code, byte code, compiled code, interpreted code, machine code, executable instructions, and/or the like may be used to control certain aspects of the operation of the analytic computing entity 65 with the assistance of the processing element 205 and operating system.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with computing entities or communication interfaces of other computing entities, user computing entities 30, and/or the like.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analytic computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The analytic computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the analytic computing entity's components may be located remotely from other analytic computing entity 65 components, such as in a distributed system. Furthermore, one or more of the components may be aggregated and additional components performing functions described herein may be included in the analytic computing entity 65. Thus, the analytic computing entity 65 can be adapted to accommodate a variety of needs and circumstances.

b. Exemplary User Computing Entity

Figure 3:
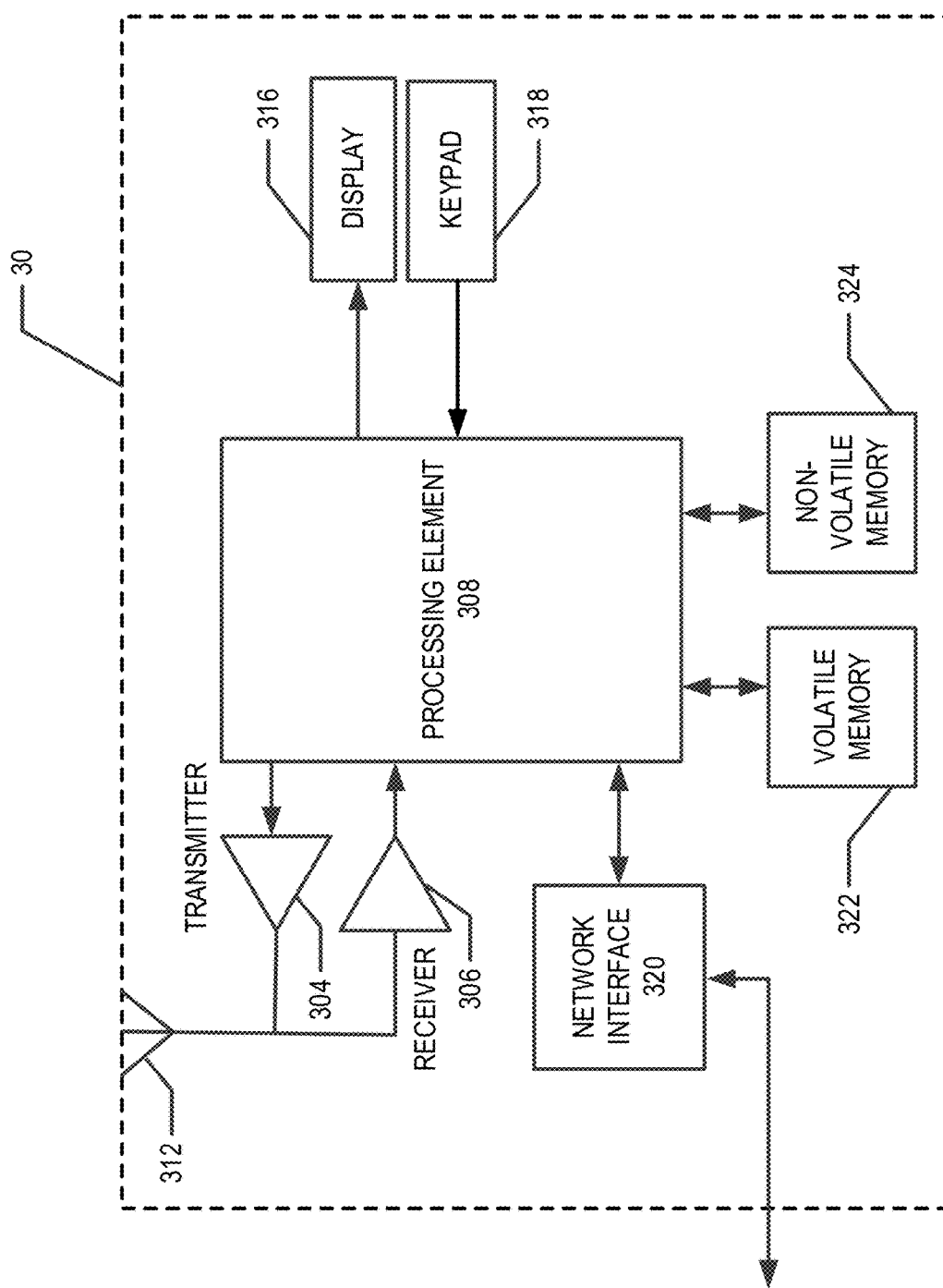
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity may be operated by an agent and include components and features similar to those described in conjunction with the analytic computing entity 65. Further, as shown in FIG. 3, the user computing entity may include additional components and features. For example, the user computing entity 30 can include a network interface 320, an antenna 312, a transmitter 304 (e.g., radio), a receiver 306 (e.g., radio), and a processing element 308 that provides signals to and receives signals from the network interface 320 and/or the transmitter 304 and receiver 306, respectively. The signals provided to and received from the transmitter 304 and the receiver 306, respectively, may include signaling information/data in accordance with an air interface standard of applicable wireless systems to communicate with various entities, such as an analytic computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/ or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the analytic computing entity 65. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Exemplary System Operation

Figure 4:
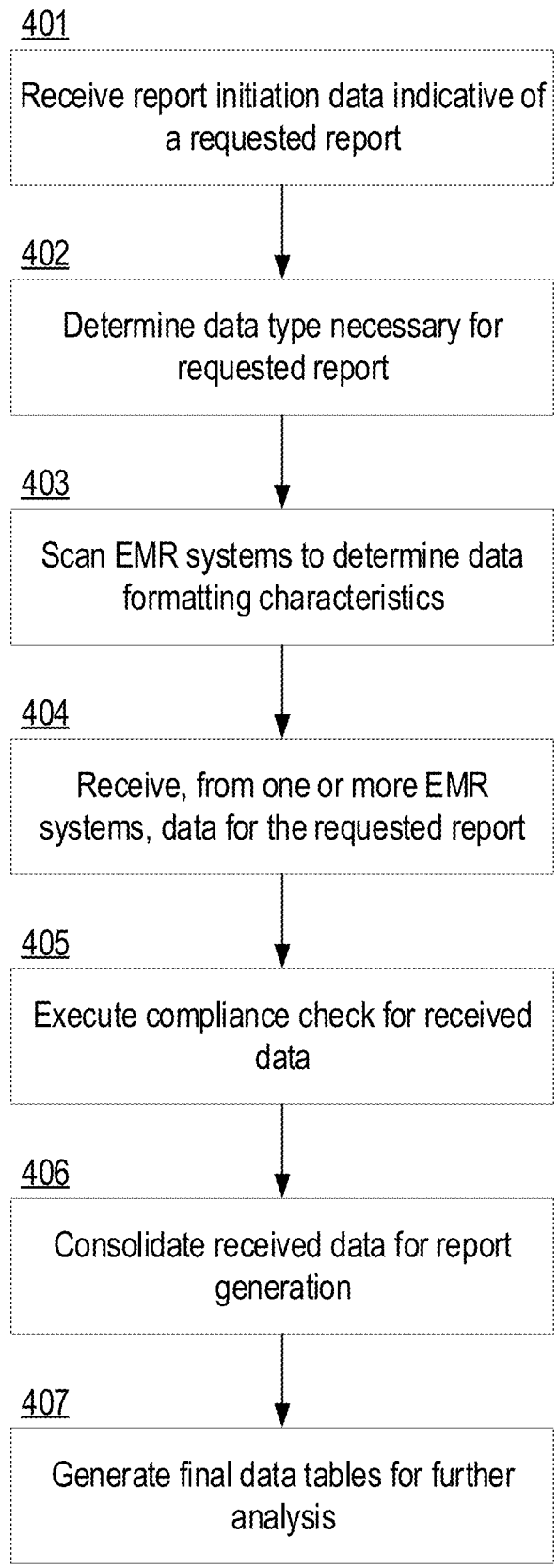
FIGS. 4-6 are flowcharts illustrating example functionalities of various components discussed herein.
Figure 5:
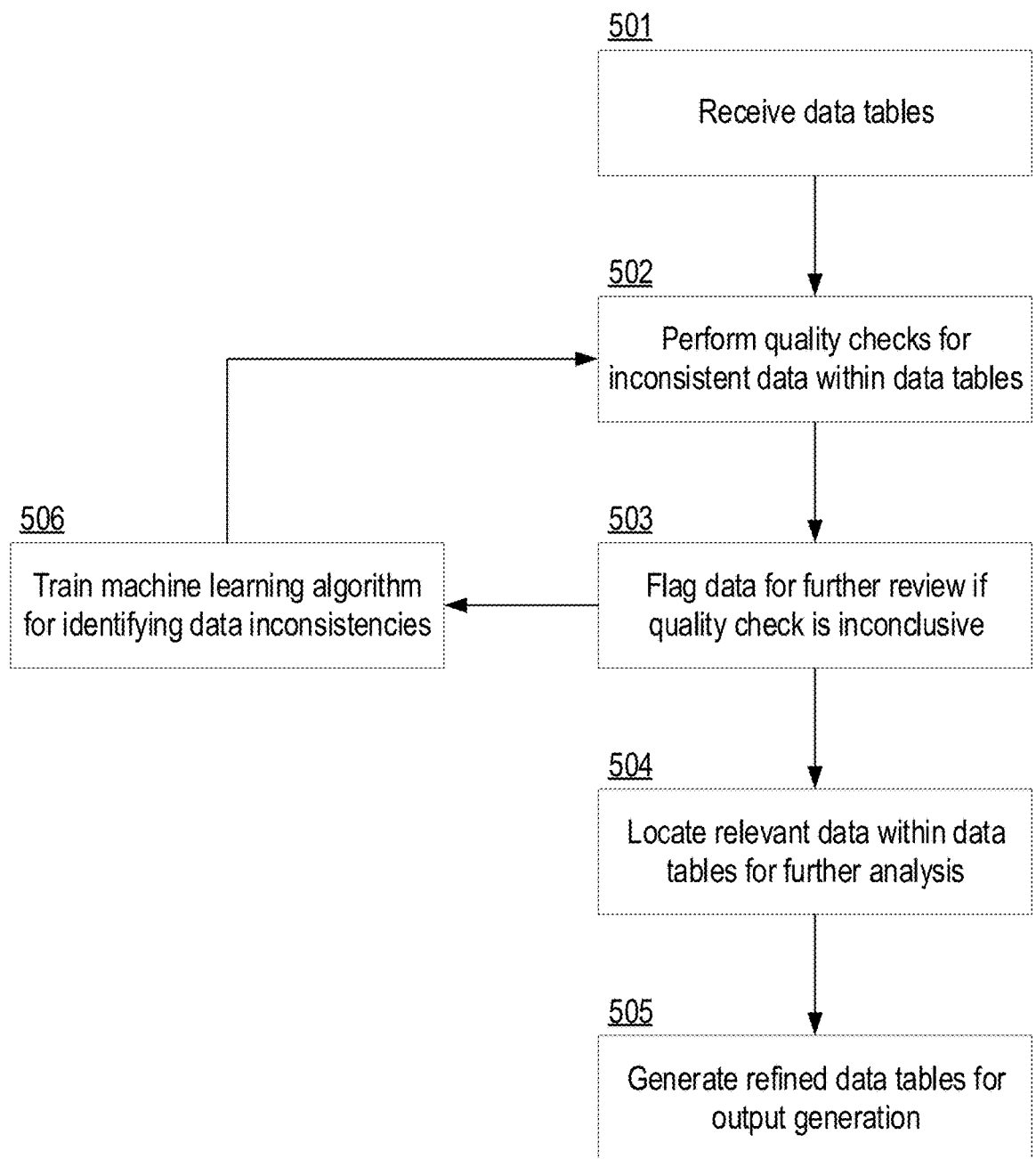
Figure 6:
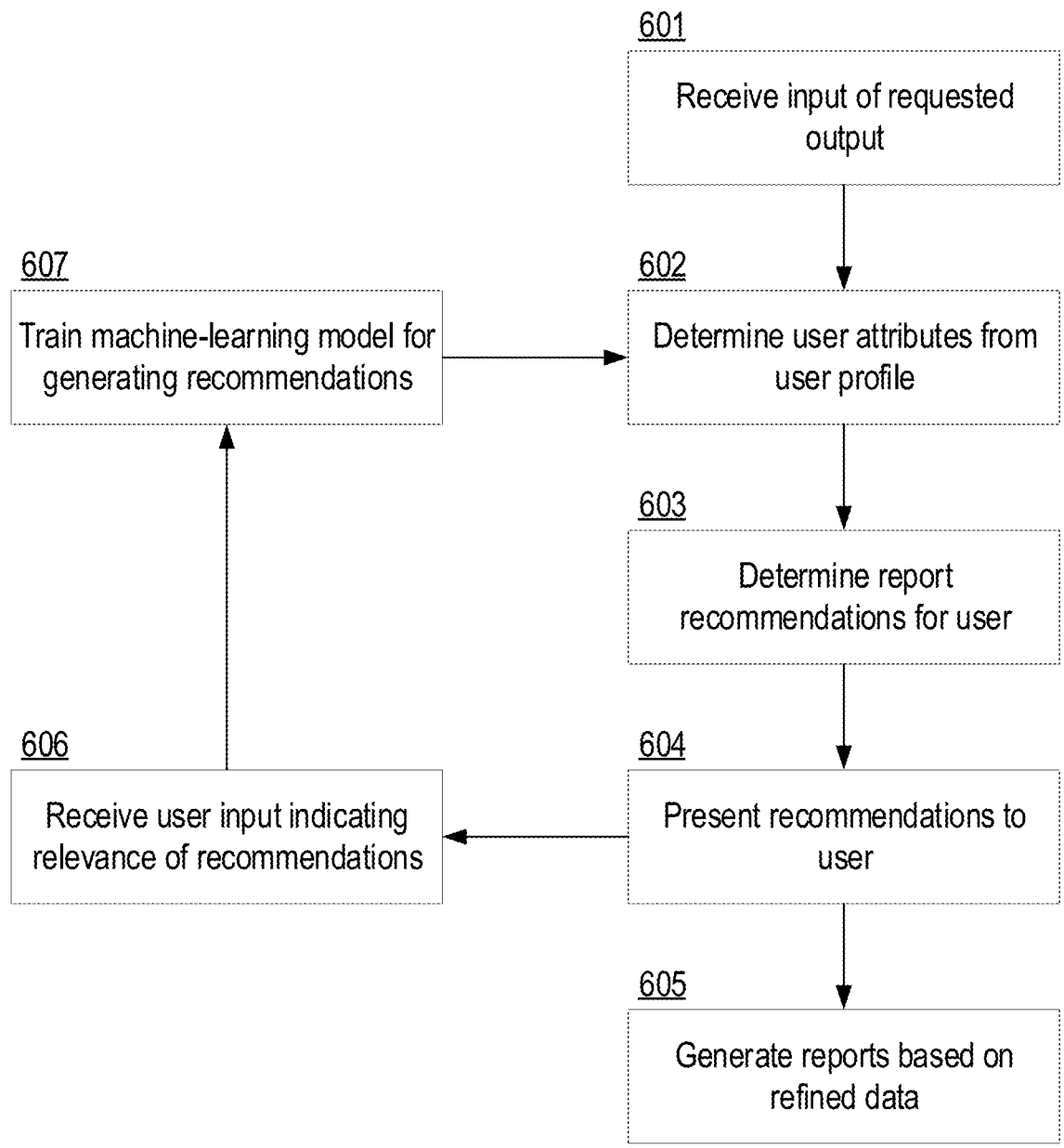
Figure 7:
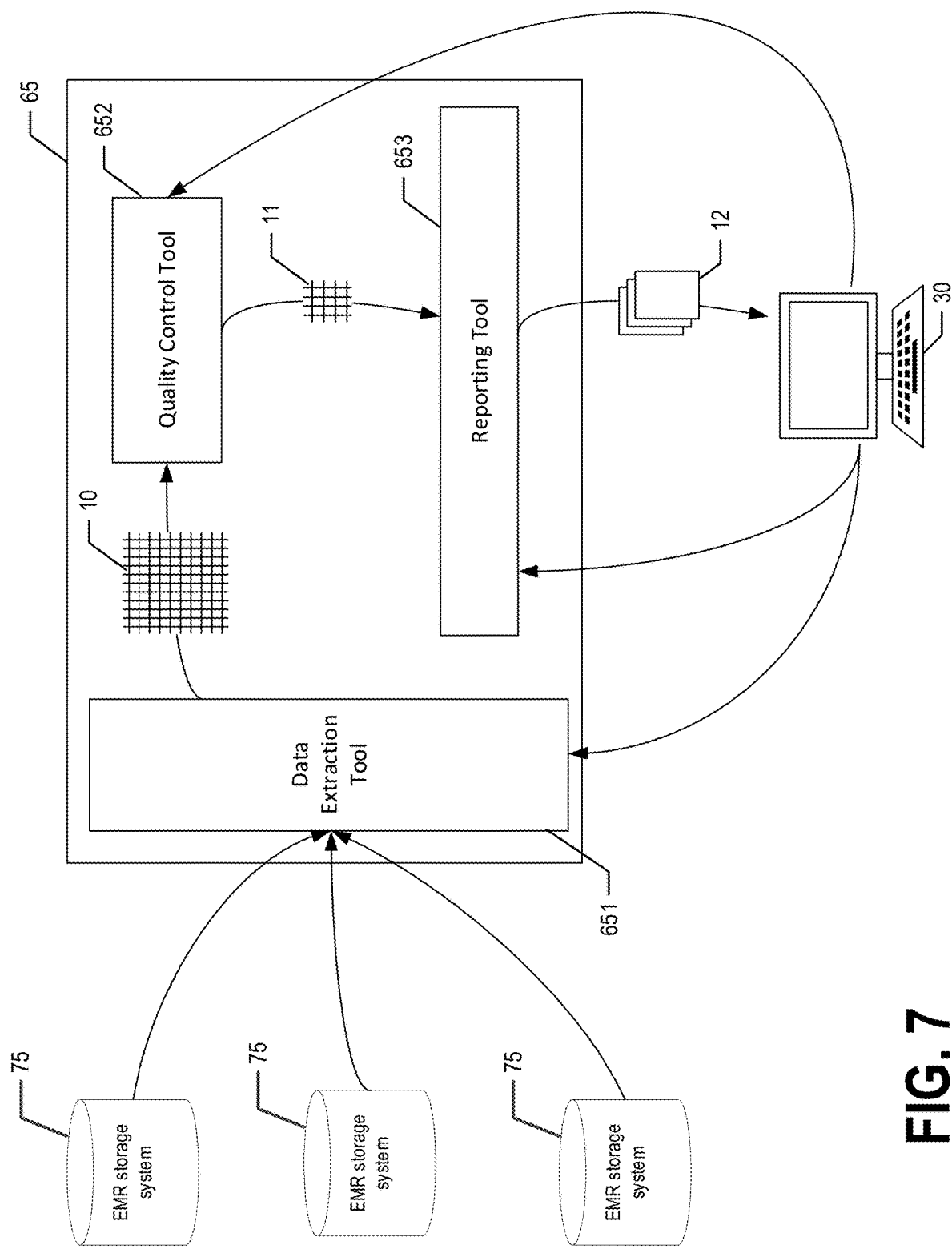
FIG. 7 is a schematic of an example configuration of an analytic computing entity according to various embodiments discussed herein.

Reference will now be made to FIGS. 4-7. FIGS. 4-6 are each flowcharts illustrating exemplary operations, steps, and processes. Moreover, FIG. 7 illustrates example data flows through an analytic computing entity 65 for receiving data from one or more health data storage systems 75, such as EMR data storage systems, processing the received data, and utilizing the received data to generate one or more reports.

a. Brief Overview

Certain embodiments consolidate the necessary steps for automatically generating and presenting bespoke research report outputs, for example, retrospective research reports. These research reports utilize clinical data that is automatically standardized according to established report requirements. Certain embodiments are configured to execute various processes for collecting retrospective data, for standardizing the retrospective data, and/or for generating reports based on the retrospective data via a single, easily navigable user interface generated and/or maintained by an analytic computing entity and accessible to one or more user computing entities (e.g., a computer of a researcher). Moreover, the system (and corresponding user interface) may be accessible to registered users (e.g., researchers), one or more of whom have user profiles comprising professional data regarding the corresponding user stored at the system. Thus, the system may utilize machine learning over time to generate suggestions for types of reports that may be relevant for a particular research project based at least in part on the type of data analyzed, the type of user accessing the system, and/or the like.

1. Technical Problem

Clinical medical data often utilized for retrospective medical research analysis is highly variable both in format and content, based at least in part on differences in data storage formats between various electronic health data storage systems, such as electronic medical record (EMR) systems, differences in data collection methodologies of the physicians generating the clinical data, and/or differences in patient need that leads to the collection of the clinical data. Moreover, clinical data is often subject to human error in inputting the data, which may result in some inconsistencies and/or inaccuracies in certain clinical data.

These inconsistencies and/or inaccuracies within data often requires significant manual data manipulation by researchers to generate reports, which can result in the introduction of yet other errors resulting from human error in performing data manipulation. Because the output of this data manipulation process may be used for patient care and/or as materials to be used to direct the improvement and/or audit of patient care, then the minimization of errors and the accuracy of the reports—up to the actual quality of the raw data is integrally important.

2. Technical Solution

To overcome at least the above-identified technical challenges, various embodiments encompass systems and methods for extracting clinical data from a plurality of health data storage systems and to standardize the retrieved data to enable the generation of reports based on data retrieved from the plurality of health data storage systems. Moreover, various embodiments utilize machine-learning based algorithms for identifying potentially inconsistent and/or inaccurate data within the extracted data to ensure such inconsistencies and/or inaccuracies are prevented from entering the final data analysis. With respect to the ultimate data analysis, various embodiments utilize further machine-learning algorithms for identifying possible and relevant data analysis that may be performed for the extracted data, for example, based at least in part on the identity and/or role of the researcher requesting retrieval and analysis thereof.

b. Data Extraction

As noted above, various embodiments are directed to systems and methods for consolidating clinical data received from a plurality of data sources (e.g., health data storage systems 75 associated with particular providers). For example, health data storage systems 75 may comprise local storage devices (e.g., databases) located at each individual provider location (e.g., a physician's office, a pharmacy, a hospital, and/or the like), or "cloud"-based storage devices, which may be remotely accessible by associated providers. In certain embodiments, a health data storage system 75 may be managed or otherwise associated with a medical claims payer (e.g., a health insurance provider), a payment integrity provider, and/or the like. In such embodiments, one or more providers may access the health data storage system 75 for retrieving data regarding individual patients, for updating data regarding individual patients, and/or the like.

In certain embodiments, health data storage systems 75 may store medical data for individual patients. The medical data may be associated with patient profiles or other patient identifiers thereby enabling providers and/or health data storage system 75 managers to retrieve the proper medical data when an individual patient visits or contacts a provider for medical care. In certain embodiments, the patient profile may comprise identifying data regarding the patient, such the patient's name and/or a unique patient identifier (e.g., an EMR-specific identifier, a globally unique identifier (such as the patient's Social Security Number). The patient profile may additionally comprise patient background data, such as the patient's age (and/or date of birth), weight, gender and/or the like. In certain embodiments, the background data may additionally comprise data identifying one or more long-term or chronic conditions experienced by the patient, however such data may otherwise be reflected in medical data associated with the patient. Similarly, the patient background data may comprise medical history data (such as the patient's personal medical history, the patient's familial medical history, and/or the like) and/or genetic testing data for the patient (which may reveal genetic markers, genetic mutations, and/or the like that may be determined relevant particularly for generation of oncology-related reports), however at least a portion of the medical history data may be reflected in the medical data associated with the patient. In various embodiments, the patient's medical data may be arranged as a plurality of individual records, each corresponding to a single visit, consultation, communication, and/or the like with a provider. In certain embodiments, individual records stored within an health data storage system 75 may comprise a textual description of the type of condition, disease, symptoms, and/or the like discussed for the record. The individual records may additionally comprise provider notes generated during the visit, consultation, and/or the like; prescriptions and/or other medication provided to the patient; results of tests performed; imaging results generated; and/or the like. Moreover, individual records may additionally comprise provider identifying data, such as a provider name, a provider location, a provider unique identifier, and/or the like. In certain embodiments, the health data storage system 75 storing data for an individual patient may leave storage artifacts within the patient data, which are indicative of the identity of the health data storage system 75 utilized to store the individual patient's medical data. Accordingly, once patient data is consolidated from a plurality of health data storage systems 75, various embodiments may be configured to distinguish between sources of the patient data (e.g., between source health data storage systems 75).

It should be understood that a provider may be a physician, a physical therapist, a nurse practitioner, a physician's assistant, or another individual providing medical care to patients. A provider may also be embodied as an organization or group of individuals providing medical care to patients (e.g., a hospital, a physician's office, an urgent care center, and/or the like).

It should be understood that various health data storage systems 75, whether associated with individual providers or groups of providers, may be characterized by unique record storage methodologies and/or data formats manifest through differing overall database indexing structures, differing underlying database storage languages, differing naming conventions for particular categories of data (e.g., data reflecting a patient's age may be storage as "age" in a first health data storage system 75, "date of birth" in a second health data storage system 75, "DOB" in a third health data storage system 75, and/or the like), differing interface structures for communicating data to/from the health data storage system 75, and/or the like. Although the unique record storage methodologies and/or data formats utilized by each of these health data storage systems 75 may be highly refined and tailored for efficient utilization of data within the respective health data storage systems 75, these unique record storage methodologies and/or data formats create potentially problematic differences between data stored by a plurality of health data storage systems 75. Thus, data remaining in a format usable by a particular health data storage system 75 is considered "raw" data as discussed herein, and may require additional processing, for example, to standardize the data into standardized report data prior to utilization of pools of data comprising data received from a plurality of health data storage systems 75.

Due at least in part to the differences between various health data storage systems 75, an extraction tool 651 of an analytic computing entity 65 as illustrated in FIG. 7 according to various embodiments may comprise a plurality of data transmission interfaces each configured to interface with one or more health data storage systems 75. These data transmission interfaces may define processes and/or methodologies by which data received via one or more data transmissions is read, translated, transcribed, and/or the like a single data set stored in memory storage areas associated with the extraction tool 651 of the analytic computing entity 65 so as to enable further processing of the data. For example, each data transmission interface may be configured to interact with health data storage systems 75 having shared data transmission protocols. In embodiments in which none of the health data storage systems 75 have shared data transmission protocols, each data transmission interface may be configured to interact with a different health data storage system 75. In certain embodiments, each data transmission interface may be characterized by a different Application Program Interface (API), accessible via unique data routing. As just one example, each API may be paired with a different associated data exchange Uniform Resource Locator (URL) where data may be transmitted from the health data storage system 75 and/or from the analytic computing entity 65 to exchange data, data requests, and/or the like between an health data storage system 75 and the analytic computing entity 65. In certain embodiments, one or more health data storage systems 75 may be configured to operate in accordance with an industry standard communication protocol, such as Fast HealthCare Interoperability Resources (FHIR) APIs so as to facilitate seamless patient medical data exchange between a plurality of systems and providers. In such embodiments, a plurality of health data storage systems 75 may be configured for communicating with the analytic computing entity 65 via one or more shared (or similar) data transmission interfaces. As discussed herein, the data transmission interfaces may be assigned to particular health data storage systems 75 upon determining a data format corresponding to the raw health data produced/transmitted by the respective health data storage system 75. For example, as discussed herein, the extraction tool 651 may be configured to scan each health data storage system 75 (e.g., scanning data received from an health data storage system 75) to determine data formats corresponding to raw health data received from each of the health data storage systems 75 so as to enable an assignment of a particular data transmission interface to each health data storage system 75 for receiving and standardizing data received from the health data storage systems 75 into a single data set configured for further processing. As just one example, the plurality of data transmission interfaces may be configured to identify and/or eliminate differences in naming conventions/terminology utilized in different raw health data sets, to generate consistent data inputs between different raw health data sets, and/or the like. It should be understood that in certain embodiments, upon connection of a new health data storage system 75 to the analytic computing entity 65 as a potential source of data for later-generated reports, a new data transmission interface may need to be constructed so as to enable proper input and standardization of raw health data received from the new health data storage system 75.

Finally, it should be understood that although many data sources in communication with the analytic computing entity 65 may be embodied as health data storage systems 75, other data sources may also be in communication with the analytic computing entity 65 in certain embodiments. For example, one or more research databases storing results of experimental research studies may additionally be in communication with the analytic computing entity 65. In such embodiments, results of experimental research studies may comprise different data than general clinical data. For example, results of experimental research studies may not include patient identifying data (but may include certain aspects of patient background data). The results of experimental research studies also may include more detailed data regarding a particular condition experienced by patients included within a corresponding research study, but may include significantly less data regarding other conditions experienced by those patients.

As yet another non-limiting example, other data sources may comprise academic and/or research-related literature storage systems, which may each store data indicative of historical academic research articles, papers, journals, and/ or the like. Medical data for individual patients (although not typically identified) and/or medical data for groups of patients may be stored in association with individual research articles and/or the like, and such medical data may be retrieved and utilized by an analytic computing entity 65 according to certain embodiments. Moreover, as will be discussed in greater detail herein, existing research articles, journals, and/or the like may contain previously generated reports, as well as data indicative of the identity (and/or type) of the researcher(s) who generated those reports. Accordingly, data retrieved from academic and/or research-related literature storage systems may be utilized for training machine-learning systems for generating recommendations of new report types and/or for generating appropriate report formatting for specific research report types.

With reference now to FIG. 4, which is a flowchart illustrating various methods, operations, and/or steps performed by an extraction tool 651 of the analytic computing entity 65, data extraction processes may await instructions from a user of the analytic computing entity 65 (e.g., a researcher looking to generate a retrospective report based at least in part on clinical data) regarding a particular type of data to retrieve. As indicated at Block 401 of FIG. 4, the analytic computing entity 65 may receive report initiation data indicative of a requested report. The report initiation data may be generated based at least in part on user input received at a user computing entity 30 which is passed to the analytic computing entity 65. The report initiation data may explicitly identify a type of report the user wishes to generate (e.g., a Kaplan-Meier survival graph for an oncology-related report, a genomics-related chart of gene expression levels of particular gene for various cancer types, genomics-related charts illustrating survival rates based at least in part on particular attributes of genomics data stored for particular patients, and/or the like). In certain embodiments, the report initiation data may additionally (or alternatively) identify characteristics of data to be analyzed. For example, the report initiation data may identify the types of patients to be included in the retrospective analysis (e.g., based at least in part on particular attributes reflected with background data of the patient, such as patient age ranges, patient genders, specific characteristics of patient medical histories, and/or the like). In other embodiments, the report initiation data may identify the types, locations, and/or the like of providers treating particular patients (e.g., individual providers, providers associated with hospitals, and/or the like), the types of treatment provided for patients (e.g., identified by treatment codes within records of medical data for individual patients), and/or the like.

Upon receiving the report initiation data, the analytic computing entity 65 of certain embodiments determines the data types necessary for a requested report, as reflected at Block 402. This process may comprise a single-step process or a multi-step process. For example, the analytic computing entity 65 may store (e.g., within one or more data storage areas, such as report databases, accessible to the analytic computing entity 65) report format data for a plurality of report types. The report format data may be stored in individual report profiles, each identifying a report type (or name), and data types necessary for generation of the report. For simple report types, the report profiles may indicate that the data needed to directly generate the report is quickly and easily identified from medical data. As a non-limiting example, a report of patients having a particular condition, arranged by age may require data indicative of a patient's conditions (to determine whether a patient has the condition of interest) as well as data indicative of the patient's age.

Such data may be directly stored within patient data within one or more data sources, and accordingly such data may be easily retrieved. However, other reports may require one or more intermediate processing steps to generate data for inclusion in a report, and accordingly corresponding report profiles may comprise data indicative of the various intermediate data types necessary, as well as data indicative of the various initial data necessary to retrieve from one or more data sources to begin generation of the report.

In certain embodiments, the analytic computing entity 65 may be configured to automatically generate one or more of the report profiles, for example, via one or more machine-learning techniques. For example, to establish an initial machine-learning algorithm, training data comprising raw data utilized to generate a report, intermediate data utilized to generate a report (if applicable), and the report itself may be provided to the analytic computing entity 65, which may be configured to generate one or more machine learning algorithms utilized to establish individual report profiles for each of a plurality reports. In other embodiments, report profiles may be generated manually, as new reports are added to the capabilities of the analytic computing entity 65.

With reference again to Block 402 of FIG. 4, the analytic computing entity 65 determines the data types necessary for generation of the requested report, within the report parameters established within the report initiation data. As discussed herein, the determined data types utilized for generation of the requested reports are later utilized for establishing table entries within a refined data table to be populated by standardized data (generated from the raw health data). In certain embodiments, as a part of determining the data types necessary for generation of the requested report, the analytic computing entity 65 generates one or more data requests each identifying specific data retrieval parameters to be utilized by one or more data sources. A separate data request may be generated for each data source to be queried (the identity of the data sources to be queried may be established based at least in part on the determined data types needed and/or the report initiation data, and accordingly the number and identity of the data sources to be queried (and thus the corresponding data retrieval requests) may be generated based at least in part on the report initiation data and/or the determined necessary data types. Similarly, the contents of the data retrieval requests, including the contents identifying the types of parameters of data to be retrieved from each data source is similarly identified and generated based at least in part on the report initiation data and/or the determined data types needed. As an example, for a report of cancer rates within teenage males associated with a particular provider, the report initiation data may indicate that only medical data relating to male patients between the ages of 13-19 should be retrieved (and/or medical data relating to male patients who received a cancer diagnosis at a time when the patient was between 13-19 years of age). Moreover, data retrieval requests may be generated for a single health data storage system 75 (or a plurality of health data storage systems 75) associated with the provider, and moreover the data retrieval requests may limit data requests to those patients associated with the identified provider. It should be understood that any of a variety of data retrieval parameters may be specified, such as the non-limiting examples of patient ages (or dates of birth), patient's provisional diagnoses, confirmed diagnoses, differential diagnoses, (with corresponding index dates, if necessary), and/or the like.

With reference to Block 403 of FIG. 4, the extraction tool 651 of the analytic computing entity 65 may be configured to scan health data storage systems 75 (or other data sources) for which data is to be requested to determine data formatting characteristics. The extraction tool 651 may then tailor the formatting of the data retrieval requests based at least in part on the determined data formatting characteristics. The data retrieval requests may thus identify the data to be retrieved from the data source based at least in part on identifiers utilized by that specific data source. Moreover, the data retrieval request may be generated to be transmitted via the appropriate data transmission protocol utilized for communicating with the specific data source.

Upon generation of the data retrieval request, the extraction tool 651 transmits the data retrieval request to the one or more data sources to cause those data sources to retrieval data matching the parameters identified within the data retrieval request. Each data source may generate a response to the data retrieval request comprising data (copies of the data) matching the data parameters identified within the data retrieval request, and may transmit the response back to the extraction tool 651 of the analytic computing entity 65.

As shown at Block 404, the extraction tool 651 of the analytic computing entity 65 receives the raw data from each of the one or more data sources (e.g., health data storage systems 75). In certain embodiments, the extraction tool 651 of the analytic computing entity 65 may directly receive data "pushed" to the analytic computing entity 65 via corresponding data transmission protocols utilized to communicate with individual data sources. In other embodiments, data may be "pulled" to the extraction tool 651 according to various communication protocols. For example, data may be provided by the data sources to an intermediate storage location, and the extraction tool 651 may then pull the data from the intermediate storage location for further processing.

Upon receipt of the data at the extraction tool 651, and before providing a user with access to the data, the extraction tool 651 may be confirmed to execute one or more compliance checks on the received data, as indicated at Block 405. For example, the extraction tool 651 may be configured to determine whether only "whitelisted" or otherwise permissibly usable data is included within the received data. As a non-limiting example, the extraction tool 651 may be configured to ensure that received data complies with applicable laws regarding patient confidentiality, by ensuring that all identifying data of a patient is removed from the retrieved data before the data is made available to the researcher. In certain embodiments, the extraction tool 651 may be configured to execute this step remotely if necessary to comply with applicable rules, laws or regulations regarding the transmission of patient identifying data. As an example, the compliance checks may be performed at an intermediate storage location prior to receipt of the data at the analytic computing entity, and/or the extraction tool 651 may be configured to transmit one or more algorithms, instructions, and/or executable program code to one or more data sources (e.g., health data storage systems 75) to pre-check retrieved data for compliance prior to ever transmitting the data at all.

In certain embodiments, the compliance check may comprise reviewing free-text fields to ensure no identifying data is contained therein (e.g., patient names, patient identifying data, and/or the like), ensuring no patient identifying data fields are included within the data, and/or the like. In various embodiments, the compliance check may be executed in accordance with machine-learning algorithms, trained to identify patient identifying data and to distinguish between patient identifying data and other codes (e.g., procedure codes, diagnosis codes, genome identifiers, and/or the like).

If it is determined that any data comprises identifying data, the extraction tool 651 may be configured to redact the identifying data from the one or more data records. This redaction may comprise removing at least a portion of the identifying data (thereby rendering the identifying data indecipherable) prior to presenting the complete data set to the user. In other embodiments, complete records comprising identifying data may be removed prior to presenting the consolidated data set to the user.

Once the data is ensured to be in compliance with applicable rules, regulations, laws, and/or the like (whether established externally to the analytic computing entity 65 or internally to the analytic computing entity 65), the extraction tool 651 consolidates the received data for report generation. As a part of the process for consolidating raw data from the plurality of data sources into standardized report data, the extraction tool 651 standardizes data formats across all data sets retrieved from the plurality of data sources. For example, different data types indicative of related characteristics of the data may be standardized to a single data type (e.g., patient age and patient date of birth may be standardized to be patient date of birth across all data sets). Moreover, data set formatting may be standardized across all data sets (e.g., HTML data, XML data, PHP data, and/or the like may all be standardized to XML data). Extraneous data may be removed from one or more data sets (e.g., artifacts of a particular health data storage system 75 may be removed if unnecessary for the chosen data analysis). In sum, data from the plurality of data sources may be standardized such that the included data may be consolidated into a single, cohesive data set. In certain embodiments, one or more machine learning algorithms may be utilized to identify corresponding data from different data sets, as well as for identifying steps for standardizing the data from the various data sources. As just one example, APIs may be utilized to receive raw data from corresponding health data storage systems 75 and to provide standardized data to the analytic computing entity 65 for further processing.

Moreover, as a part of standardizing the data across data sets received from the plurality of data sources, the extraction tool 651 may be configured to generate one or more summary statistics of the overall, consolidated data set. The summary statistics to be generated for the consolidated data set may be identified based at least in part on the report initiation data received from the user (e.g., identifying the type of report requested). For example, based upon a request for a Kaplan-Meier survival curve report, the extraction tool 651 may generate data indicative of an earliest date of diagnosis from patients reflected within the consolidated data set and/or may generate a timescale until an identified index date. Such summary data may be generated and/or identified utilizing machine-learning algorithms, for example, configured to parse medical data received for each a plurality of patients to identify relevant data indicative of a diagnosis of a particular condition of interest, and to identify dates associated with the identified diagnosis.

In certain embodiments, the extraction tool 651 is further configured to ensure that data is consistent within the entirety of the consolidated data set. For example, if a user has requested that data reflect a stratification based on characteristics of a particular condition (e.g., stratification of cancer-related data by stage), the extraction tool 651 ensures that sufficient data is included within each stratification to provide sufficient data to extrapolate general characteristics of each stratification (the data within each stratification satisfies the law of small numbers). Upon identifying inconsistencies and/or logical fallacies that arise from the data set, the extraction tool 651 may generate one or more alerts for the user, such that the user can consider adjusting the parameters within the report initiation data prior to generating the report.

As reflected at Block 407, the extraction tool 651 generates one or more finalized data tables 10 (represented schematically in FIG. 7) for further analysis by the analytic computing entity 65. These finalized data tables 10 comprise consolidated and standardized data received from one or more separate data sources that may be utilized to generate one or more reports based on data received from a plurality of data sources.

c. Quality Control of Extracted Data

The finalized data tables 10 produced by the extraction tool 651 may be passed to a quality control tool 652 of the analytic computing entity 65 as shown in FIG. 7. Generally, the quality control tool 652 is configured to ensure data integrity of the generated data tables by taking a remedial action upon the identification of data of questionable validity.

With reference to FIG. 5, which illustrates various steps, processes, and/or methods performed by the quality control tool 652, the quality control tool 652 is initiated upon receipt of data tables, for example, from the extraction tool 651, as indicated at Block 501.

As indicated at Block 502, the quality control tool 652 performs one or more quality control checks of the data tables. These quality control checks may be performed on each individual data entry (e.g., by crawling each data table and applying the quality control checks for each individual data cell) and/or may be performed on the data tables in the aggregate. As an example, the quality control checks may ensure that patient ages reflected in the data table are reasonable. The quality control checks may utilize a threshold (e.g., 200 years old) to apply remediation techniques, such as automatically flag any patient ages deemed unreasonable/impossible (e.g., data indicating that a patient is greater than 200 years old may be flagged as likely erroneous). As yet another example, the quality control checks may utilize thresholds based on combinations of data to identify potentially erroneous data (e.g., data indicating that a patient aged 5 years old who identifies as female has prostate cancer may be flagged as likely erroneous) and to apply remediation techniques thereto (e.g., remove data entries containing potentially erroneous data, replace potentially erroneous data, and/or the like). The quality control tool 652 may be configured to execute the quality control checks based at least in part on user defined quality control rules (e.g., a patient age threshold, particular medical requirements for certain conditions, and/or the like). In other embodiments at least some of the quality control rules may be automatically generated and/or modified by the analytic computing entity 65, for example, based at least in part on machine learning algorithms. For example, over time, the quality control tool 652 may analyze various data sets and apply remedial actions, such as flagging particular data as potentially erroneous for further review by the user (as indicated at Block 503). The quality control tool 652 may monitor the user's response to the flagged data, to determine whether the user agreed that the data was erroneous (e.g., by the user modifying the data, by the user deleting the data entirely, and/or the like) or to determine whether the user disagreed and found the data accurate. This data may be utilized as training data over time for the quality control tool 652 to construct a machine-learning algorithm to learn to identify erroneous data within data tables.

As yet other examples of quality control rules that may be applicable for various embodiments, the quality control tool 652 may be configured to perform consistency checks within longitudinal patient data to ensure data integrity. For example, treatment for a condition should not begin prior to the initial diagnosis for the condition, particularly if the treatment and condition are performed by the same provider. As a non-limiting example, chemotherapy treatment for a patient's cancer should not precede an initial cancer diagnosis for the cancer. Finding inconsistent longitudinal data (such as dates indicating the occurrence of various processes occurring out of order) may be flagged as potentially erroneous.

As yet another example, the quality control tool 652 may perform sense checking between an identified diagnosis event and a subsequent mortality to replicate oncologist intelligence as part of the quality control process. As a specific example, the quality control tool 652 may be configured to review various data sets to determine consistency therebetween. For two data sets reflecting patients having different stages of cancer (or another disease), the quality control too 652 may be configured to determine whether the data sets are properly labeled, for example, by detecting whether the more serious or life-threatening stage of the reflected disease is characterized by a shorter life expectancy than less serious and/or less life-threatening stages of the same disease.

In certain embodiments, the quality control checks may further comprise checks of particular diagnosis codes, procedure codes, genetic codes, and/or other identifiers utilized to uniquely identify particular aspects of patient's treatment and/or condition. These checks may be performed utilizing specific data within the provided data tables, such as data indicative of unique codes identified within particular data records, as well as descriptions (e.g., free text-based descriptions, such as those that may be generated by a provider during a clinical check-in with a patient). This data may be compared with code indexes, such as ICD-10 procedure code indexes, ICD-10 diagnosis code indexes, genetic terminology indexes, and/or the like. These indexes may be stored locally in association with the analytic computing entity 65 and/or these indexes may be accessed from external data resources maintaining updated versions of each of these indexes.

As indicated at Block 503 of FIG. 5, the quality control tool 652 is configured to perform remedial action for potentially erroneous data, such as to flag potentially erroneous data for further review. This is just one example of potential remedial actions that the quality control tool 652 may be configured to take according to certain embodiments. As other non-limiting examples, the quality control tool 652 may be configured to search other data relating to a potentially erroneous data record, to identify correct versions of the potentially erroneous data. For example, if a patient's age is incorrectly indicated as 233 years old, the quality control tool 652 may crawl other data relating to the same patient and identify whether the patient's age is indicated elsewhere (e.g., within another data record relating to the same patient). Upon identifying another age, the quality control tool 652 may determine a confidence score for the age (e.g., using machine learning tools that determine whether the same age is utilized more than once, considering conditions associated with the patient, and/or other data regarding the patient), and if the confidence score satisfies a defined criteria (e.g., a defined threshold), the quality control tool 652 may update the data to reflect the newly identified corrected data (e.g., replacing the patient's 233 year old age with the newly discovered patient age). In various embodiments, the quality control tool 652 is further configured to flag the corrected data for the user to review.

As yet another example, upon identifying potentially erroneous data, the quality control tool 652 may be configured to remove all records determined to be potentially tainted by the potentially erroneous data from the data tables. For example, if the patient's age is irreconcilably erroneous, all records associated with that single patient may be removed. As another example, if a number of records associated with a patient relate to an upper respiratory infection diagnosis, and yet data indicates the patient had an onset of symptoms on January 5, and the symptoms were resolved by January 3 (2 days before the onset of the symptoms), all records relating to the upper respiratory infection may be removed, but other records relating to the patient (e.g., a prostate cancer diagnosis) may remain within the data tables. Again, processes for identifying these potentially erroneous data and for determining whether the data is reconcilable may be made utilizing one or more machine-learning algorithms learning based at least in part on user input addressing other erroneous data identifications.

With reference again to FIG. 5, Block 506 represents steps for training a machine learning algorithm to identify potentially erroneous data via the quality control tool 652, such that later quality control tool 652 uses may be more precise in identifying potentially erroneous data.

Once the quality control review has been completed, the quality control tool 652 may be configured to refine data included within the data tables based at least in part on the report type requested (e.g., as identified within the report identification data). Relevant data may be located within the data tables, for example, by identifying patient data records deemed relevant for the generation of the requested report as indicated at Block 504. As a non-limiting example, for an oncology data analysis report, the quality control tool 652 may be configured to crawl the data included within the data table to remove other, non-cancer related diagnosis data (e.g., an upper respiratory infection occurring for a patient prior to an initial cancer diagnosis). Recognizing that the process of refining the data tables to remove potentially irrelevant data is associated with some level of risk of falsely removing relevant data that is erroneously deemed irrelevant, the quality control tool 652 may be configured to utilize confidence scoring to determine whether a particular data record should be removed from the data table during data refinement processes. As a non-limiting example, the quality control tool 652 may utilize machine-learning based processes to distinguish between data deemed relevant to a particular report and data deemed irrelevant to a particular report. These machine-learning based processes may be trained utilizing any of a variety of training data types that may be indicative of data deemed relevant for a particular report type. As non-limiting examples, training data for these machine-learning based processes may comprise one or more of: tables and/or outputs from open-access research publications, data reflecting a user's preferences when selecting and/or creating research reports (e.g., a user may provide data indicative of a variety of preferences for different reports, for example, reports to be utilized in different contexts), data indicative of guidelines/requirements for reports published by one or more entities (e.g., report requirements for conferences, national registries, and/or the like). This machine-learning model for distinguishing between relevant and irrelevant data may comprise a multi-level machine-learning model. A first level may be configured specifically to determine what types of data are relevant to a particular analysis associated with the generation of a particular report type. For example, the first level of the machine learning model may be configured to determine particular data necessary for the generation of the report type (e.g., a report type for charting the duration of a particular condition would require data indicating the initial diagnosis and data indicating a final date of treatment). This first level of the machine-learning model may be trained utilizing data of historical reports (e.g., based at least in part on reports generated previously by the analytic computing entity 65; reports retrieved from one or more data sources, and/or the like).

A second level of the machine learning model may be configured to identify data records indicative of the data deemed necessary within the first level of the machine learning model. Utilizing the results of the first level of the machine-learning model, the second level of the machine learning model identifies characteristics of particular data records deemed relevant for the particular report type requested. When applying the second level of the machine learning model to the data tables, the quality control tool 652 may be configured to generate a confidence score when determining whether each data record is deemed relevant or irrelevant to a particular data analysis. For example, upon identifying a particular data record as relevant, the quality control tool 652 may be further configured to generate a confidence score associated with the determination of relevance of the data record. These confidence scores may then be utilized with corresponding rules designating when a particular data record should be removed (e.g., a designation of "irrelevant" together with a sufficiently high confidence score may cause the quality control tool 652 to remove the data record during data refinement of the data tables).

Figure 8:
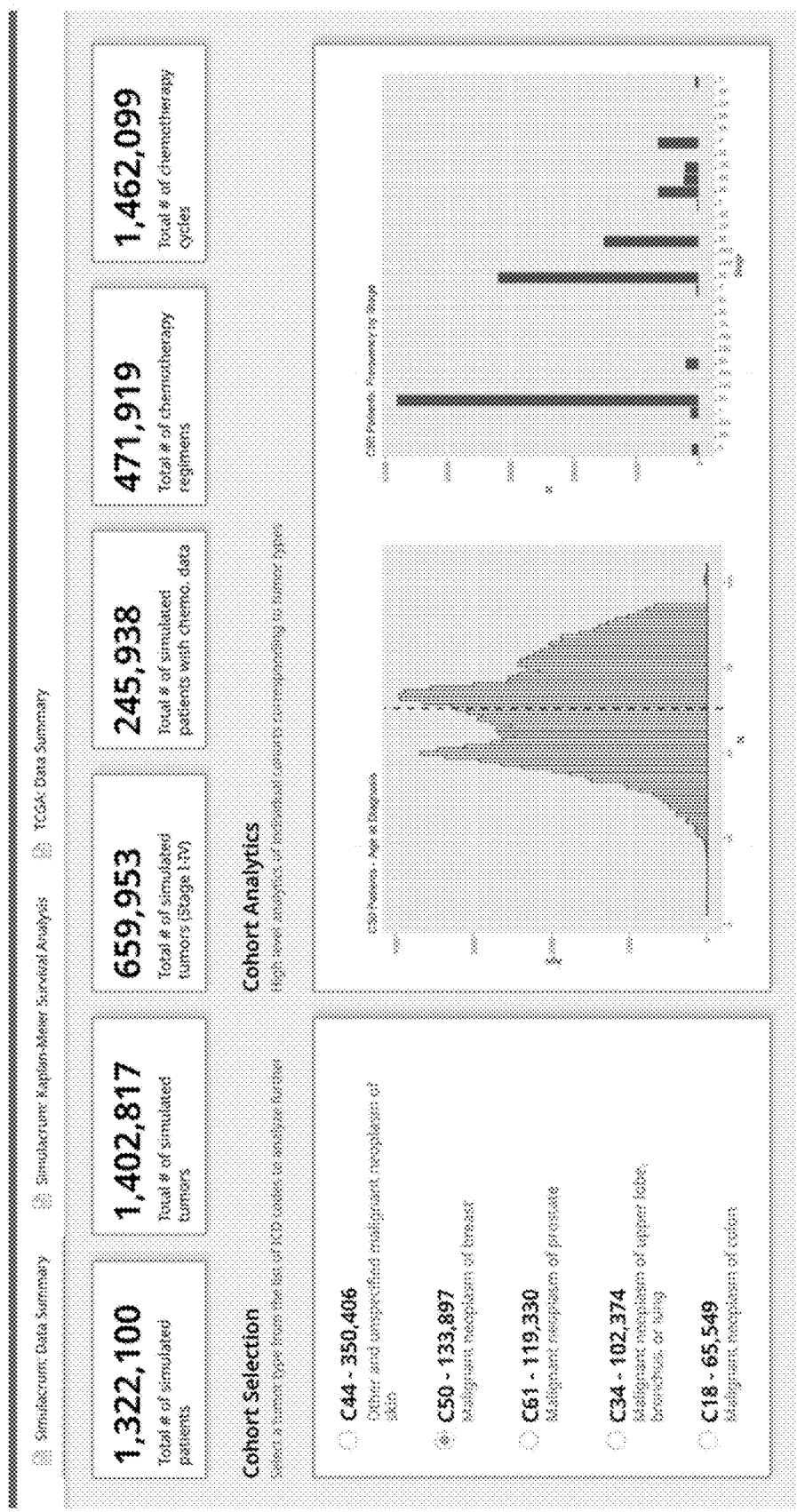
FIGS. 8-10 are example graphical interface outputs of various embodiments as discussed herein.
Figure 9:
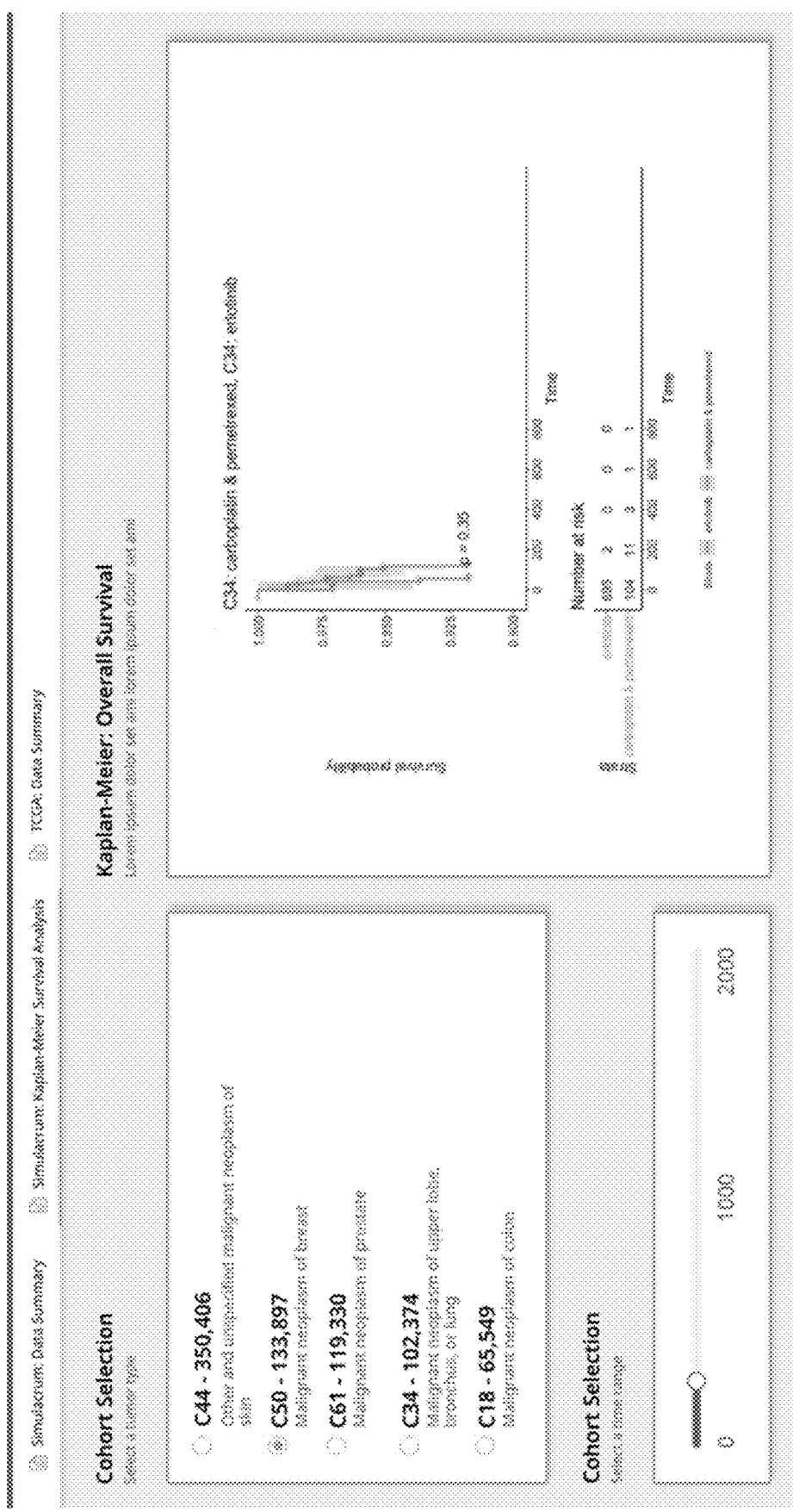
Figure 10:
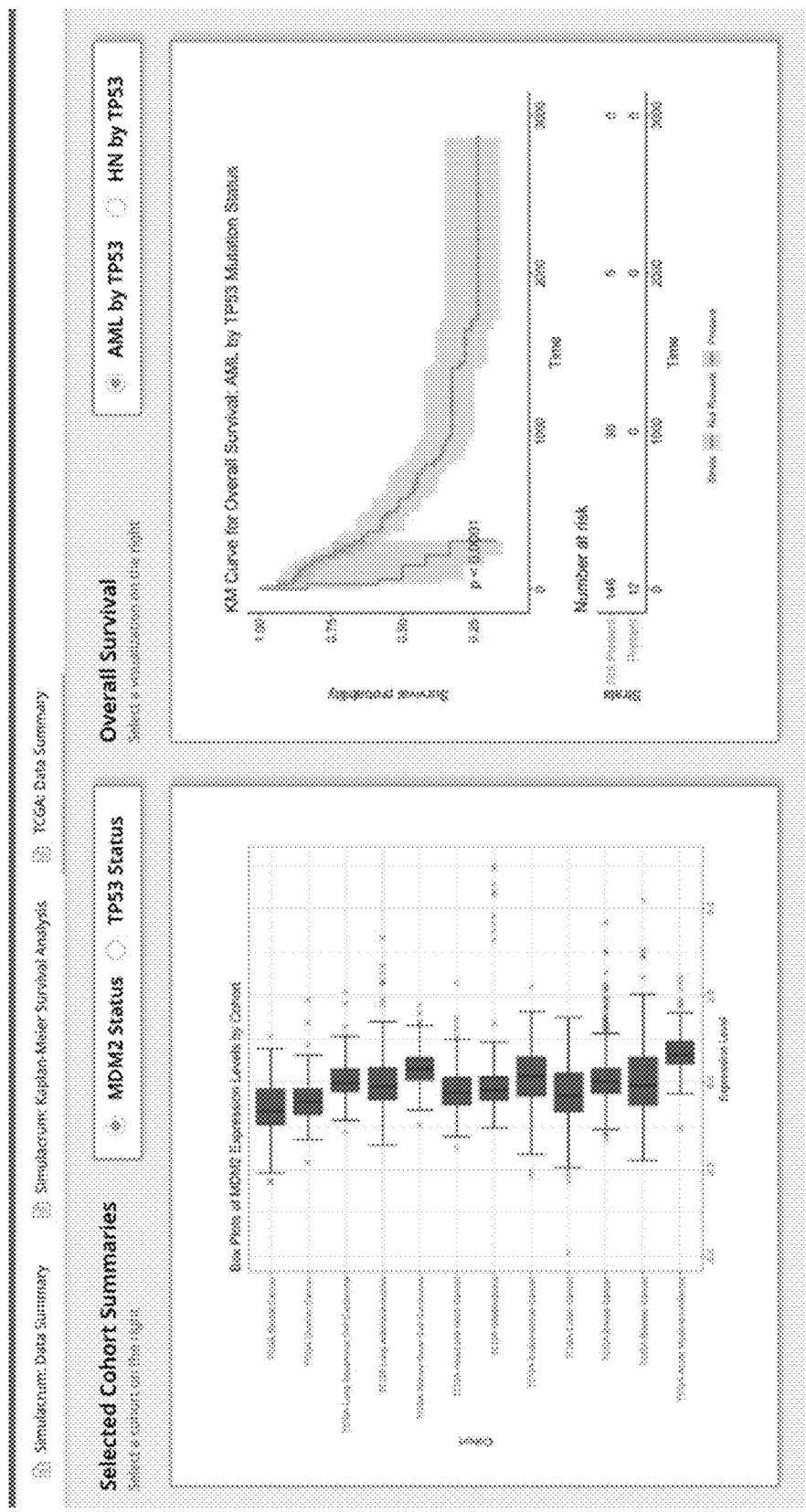

Finally, as reflected in Block 505, the quality control tool 652 generates refined data tables 11 (represented schematically in FIG. 7) resulting from the various quality control processes performed by the quality control tool 652. These refined data tables 11 comprise standardized report data to be utilized to generate the requested reports, with assurances that standardized report data included within the data tables (and the generated reports) are accurate and relevant. As will be understood, because the quality control tool 652 both ensures the accuracy of data included in further analyses, and refines the data tables from the raw state when they are first consolidated from data received from a plurality of data sources, the quality control tool 652 automatically generates refined data tables 11 containing quantities of data that are easily processible by the reporting tool 653 of the analytic computing entity 65. The standardized report data contained within the refined data tables 11 is sufficiently standardized and consistent so that the reporting tool 653 may generate clean data reports 12 (shown schematically in FIG. 7, and examples of which are shown in FIGS. 8-10) without significant (or any) user intervention, and the refined data tables 11 are sufficiently well refined that extraneous data originally included in the consolidated data table is removed so as to reduce the processing resources required to read the refined data tables 11 and to generate reports 12 based at least in part on the same.

d. Optimal Output Selection

Finally, the refined data tables 11 are passed to a reporting tool 653 of the analytic computing entity 65 for generation of the requested reports 12. With reference to FIG. 6, which illustrates various steps, methods, and/or processes performed by the reporting tool 653 of the analytic computing entity 65, the reporting tool 653 receives the refined data tables 11 from the quality control tool 652 as indicated at Block 601. Using the refined data tables 11, the reporting tool 653 is configured to generate one or more reports as requested by the user (e.g., via the report initiation data generated at the user computing entity 30). Moreover, the reporting tool 653 is configured to provide additional report suggestions based at least in part on the type of user requesting those reports and/or the type of reports requested. Thus, as indicated at Block 602 of FIG. 6, the reporting tool 653 of the analytic computing entity 65 is configured to determine user attributes of the requesting user (as reflected within user attribute data), from a user profile associated with the requesting user. As discussed herein, each user of the analytic computing entity 65 may have a corresponding user profile, including a unique user name and password collectively utilized for accessing the analytic computing entity 65 (it should be understood that other log-in mechanisms may be utilized in alternative arrangements, such as multi-factor authentication, Single-Sign-On (SSO) configurations, and/or the like). The user profile may additionally comprise biographic data for the associated user, such as a user's name, company/institution/entity affiliation (if applicable), contact information (e.g., email address, phone number, instant messaging contact information, and/or the like), a user's title, a user's education level (e.g., level of education, type of degree(s) received, and/or the like), and/or the like. In certain embodiments, such as those embodiments in which the reporting tool 653 of the analytic computing entity 65 is configured to access potential data sources external to various health data storage systems, the reporting tool 653 may be configured to retrieve identifying information associated with the user (e.g., via the user profile) and utilize the identifying information to retrieve additional data from external data sources. For example, the reporting tool 653 may be configured to retrieve data from one or more educational databases (e.g., which may include data indicative of one or more degrees earned by the user), one or more human resources databases (e.g., which may include data indicative of a job title associated with the user), one or more social networks (e.g., which may comprise additional data indicative of degrees earned, job titles associated with the user, years of professional experience, industry associations, and/or the like), and/or one or more additional external data sources.

In certain embodiments, the reporting tool 653 may refer to a look-up data table and/or a defined ruleset (which may be generated at least in part based on input received from researchers and/or clinicians) to determine a number of variants of the required output that are feasible, based at least in part on the user's prior input identifying requested output reports and/or based at least in part on the data tables generated through the quality control process discussed above. As just one example, for KM-curves requested for a report, 1, 3, and 5 year KM curves may be generated for reports. However, such data may additionally support 2-year and 4-year KM curves, if desired by the user (at present, submissions to the National Institute for Health and Care Excellence (NICE) in England for evaluations of new drugs may require submission of a 2-year KM curve). It should be understood that in certain embodiments, the data included within the data tables generated through the quality control process discussed above may support one or more additional reports of entirely different report types than those requested.

Based at least in part on a determination of what additional reports may be supported by the disclosed data, the reporting tool 653 of the analytic computing entity 65 generates additional output reports. As reflected at Block 603 of FIG. 6, the reporting tool 653 determines report recommendations for the user, prior to presenting additional available reports for user selection (as reflected at Block 604). Determinations of the report recommendations for the user may be generated by the reporting tool 653 utilizing machine-learning algorithms, considering the type of report requested, whether the report was requested to be of publication-quality, characteristics of the user (as determined based at least in part on data within the user profile and/or one or more external data sources), and/or the like. In certain embodiments, each of the additional reports may receive a relevance score, for example, based at least in part on the user, the user's attributes, the report requested by the user, and/or the like. The reporting tool 653 may then utilize a threshold to determine whether a particular additional report is designated as a recommended additional report. For example, the reporting tool 653 is configured to determine that additional reports having a relevance score (determined based at least in part on a machine-learning based algorithm) above a threshold relevance score level, are deemed recommended additional reports to be presented to the user. As discussed in greater detail herein, the machine-learning algorithm may be trained via data indicative of reports presented to prior users as well as user feedback indicating whether the generated reports were deemed useful to the users. The determinations of report recommendations may be made prior to the generation of the additional report outputs (e.g., so as to conserve processing resources). Only those reports deemed relevant may be generated by the reporting tool 653. However, in other embodiments, the reporting tool 653 may be configured to generate a plurality of reports determined to be supported by the data included within the data tables output from the quality control process discussed above prior to a determination of relevance to the user. The reporting tool 653 may then utilize attributes of the generated reports within the machine-learning algorithm to determine whether the output reports are relevant to the user.

In yet other embodiments, the reporting tool 653 may first utilize one or more defined rulesets to determine instances in which particular reports are deemed relevant and/or irrelevant for a particular user. Such defined rulesets may be utilized as a low-processing resource requirement, initial filter of the output reports prior to presenting the same to users. In certain embodiments, the initial filter may be applied prior to application of the machine-learning based filtering, concurrently with the machine-learning based filtering, and/or after application of the machine-learning based filtering. As just one example, defined rulesets for KM curve reports for various stages of a particular type of cancer may indicate that additional KM curves for additional cancer stages may be deemed relevant reports for a user in instances in which the data tables output from the quality control process discussed above indicate that multiple cancer stages have similar survival rates (e.g., the data tables indicate that Stage II and Stage III cancers have a survival rate that is within 5% of one another).

Upon presenting the recommended additional report outputs to the user (e.g., as a portion of a graphical user interface), as indicated at Block 604 of FIG. 6, the reporting tool 653 may further present one or more user interfaces requesting user input indicative of the perceived utility of the one or more additional report outputs to the user. For example, the user interface may provide users with a selection of one or more options, such as a binary "useful" or "non-useful" set of selections, a graduated "very useful," "somewhat useful," "somewhat non-useful," or "non-useful" set of selection, and/or the like. Other embodiments may request other forms of user input, such a free-text input. In yet other embodiments, no user input is requested, however the reporting tool 653 may track whether each additional output report is downloaded, saved, viewed, and/or the like by the user. The user input (or metadata utilized as a proxy for user input) is received by the reporting tool 653 as indicated at Block 606. The reporting tool 653 may input the received user input (together with data indicative of the report to which the user input applies) as training data for machine-learning algorithms utilized to generate recommendations of additional reports for users, as indicated at Block 607. As discussed above, this training data is utilized to tailor the machine-learning model utilized to provide recommendations of additional reports to users. In certain embodiments, the generated training data is utilized in a user-specific manner, such that future recommendations for the particular user who provided user input on one or more additional reports is tailored based at least in part on training data generated for that user. In other embodiments, the training data may be utilized in a generalized fashion, for example, such that training data is applicable across users, such that recommendations of one or more additional reports may be generated for users based at least in part on training data generated based at least in part on user input from users having similar backgrounds and/or the like.

With reference to Block 605 of FIG. 6, the reporting tool 653 generates finalized reports as requested by the user and/or as identified as relevant by the user (e.g., selected from the one or more additional reports recommended by the reporting tool 653). In certain embodiments, the reporting tool 653 may be configured to automatically generate reports in an appropriate format based at least in part on an intended final use of the report by the user (e.g., as identified by the user when initially requesting the report). Accordingly, the reporting tool 653 is configured to determine an intended final use of the report by the user (e.g., based at least in part on user input provided by the user, based at least in part on a determined likely final use by the user, which may be identified via an algorithm (e.g., a machine-learning algorithm) identifying a likely final based on characteristics of the user, characteristics of the reports requested, characteristics of the additional reports selected, and/or the like).

Once the intended final use is identified and/or predicted, the reporting tool 653 is configured to query a formatting database comprising data indicative of report formatting rules for one or more intended final uses. At least a portion of the formatting database may be populated based at least in part on user input (e.g., report formatting requirements for internally-used reports for a particular organization may be populated manually) and/or by retrieving formatting requirements from one or more external sources. For example, the formatting database may be configured to receive formatting requirement data from various research journals for tables, charts, graphs, and/or other report styles. The formatting requirement data may be pushed from the external sources as updates are provided, or the formatting requirement data may be pulled (e.g., via a periodic query transmitted to the external source) upon determining that updates to the formatting requirement data is provided.

Upon identifying relevant formatting requirements for the reports, the reporting tool 653 generates the final reports utilizing relevant data from the data tables generated through the quality control process discussed above and the relevant report formatting requirement data retrieved from the formatting database, as indicated at Block 605. These generated reports are then provided as output to the user. For example, the reports may be graphically displayed via a graphical user interface to the user. In certain embodiments, the reports may be stored as a report file that is provided to the user's user computing entity 30. In various embodiments, the reports may be stored at the analytic computing entity 65, for example, in association with a user profile corresponding to the user. Thus, the user may have easy access to the generated reports at a later date via the user's user profile. In certain embodiments, graphical reports generated and presented to a user may encompass illustrated graphs (e.g., KM curves, bar graphs, pie charts, and/or the like), alphanumeric text-based tables presented graphically to a user, bulleted lists presented graphically to a user, automatically-generated prose presented graphically to a user, and/or the like.

FIGS. 8-10 illustrate example graphical output reports that may be generated according to various embodiments. As illustrated therein, various Kaplan-Meier analysis reports may be generated and illustrated graphically for a user, for example, in a format adequate for usage within one or more research reports. As illustrated in FIGS. 8-10, the analytic computing entity 65 may be configured to generate reports comprising graphics (e.g., charts, graphs, and/or the like) indicative of data included within the refined data tables, textual summary data, and/or the like. As noted, certain reports generated by the analytic computing entity 65 may be specifically formatted and configured for use within final research reports to be published within papers, journals, and/or the like. Accordingly, relevant data is presented in a fixed manner capable of easy reproduction in print. However, as shown specifically in FIGS. 8-10, the reports generated according to certain embodiments may comprise one or more interactive features, for example, enabling users/readers of the final report to focus on particular aspects of a report. For example, an interactive features may be embodied as a plurality of alternatively-selectable radio buttons configured to show different data sets within a graphic, a slider bar configured to change the portion of a particular data set represented within a graphic, and/or the like. It should be understood that any of a variety of graphics e. Training Machine Learning Algorithms As will be recognized, machine learning algorithms as discussed herein may be implemented in association with artificial neural networks are designed to recognize patterns using machine learning algorithms. Typically, the patterns they recognize are numerical, contained in vectors, into which real-world data is translated. With regard to embodiments of the present invention, the real world data may comprise training data including data indicative of whether a particular user found one or more additional reports to be helpful (e.g., based on user input), data indicative of characteristics of a user (e.g., based at least in part on data included within a user profile), and/or the like. As just one example, the desired features of the relevant data are extracted and formatted into multidimensional vectors to be input into one or more neural networks. The neural networks comprise one or more layers that receive, amplify or dampen the input, and provide an output. For multiple layers, each layer's output is simultaneously the subsequent layer's input. With regard to determining a relevance of a particular recommended output, for example, a relevance score may be generated for each potential output report by determining vector distances between numerical representations of attributes of each potential additional report and relevant attributes of reflected within the neural network model, generated based at least in part on the training data as discussed herein.

As will be recognized, training and/or retraining a neural network involves providing a training dataset to the neural network. The training dataset contains the target output or variable (e.g., the additional reports) that the machine-learning model is to eventually predict along with the related features. The neural network detects patterns in the training dataset that map the input information/data attributes from the feature sets to the target output or variable and captures these patterns. The resulting neural network is then able to generate relevance scores for recommended additional reports, even for scenarios in which the exact combination of claim attributes has not been analyzed previously. The scores can be determined in real-time or near real-time— such as when a new request for a report is provided by a new user.

As a result of the training or retraining, one or more neural networks are generated to subsequently generate relevance scores of previously unconsidered recommended reports.

In one embodiment, the analytic computing entity 65 can retrain the neural network on a regular or continuous basis or in response to certain triggers. This may be necessary as additional/new data types are introduced into raw data (which may ultimately culminate in the availability of new, previously unconsidered reports).

As will be appreciated, the hidden and/or weak correlations found as a result of the neural network are simply not practical for human-implementation. In addition to outputting risk scores of previously unconsidered claims, the neural networks can be retrained on a continuous, regular, or triggered basis.

VI. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for automatically standardizing data received from a plurality of electronic health data sources to generate one or more graphical reports, the method comprising:
   receiving, by one or more processors, report initiation data identifying one or more requested reports and identifying a user profile associated with the report initiation data;
   receiving, via a plurality of data transmission interfaces, raw health data from a plurality of health data storage systems, wherein the raw health data from each of the plurality of health data storage systems is received through corresponding data transmission interfaces collectively configured to standardize the raw health data into a single data set;
   applying, via the one or more processors, a machine-learning quality control check to identify inaccurate data included within the raw health data;

upon identifying inaccurate data within the raw health data, remediating, via the one or more processors, the inaccurate data within the raw health data;

after remediating the inaccurate data within the raw health data, generating, via the one or more processors, a refined data table comprising standardized report data relevant for the one or more requested reports, wherein the standardized report data is generated from the raw health data received from the plurality of health data storage systems;

determining, via the one or more processors executing a machine-learning algorithm, one or more additional reports supported by the refined data table;

determining, via the one or more processors, a relevance score for each of the one or more additional reports based at least in part on user attribute data reflected within user profile data associated with the identified user profile;

determining, via the one or more processors, one or more recommended additional reports selected from the one or more additional reports based at least in part on the relevance score generated for each of the one or more additional reports;

generating one or more of the requested reports based at least in part on the refined data table; and generating a graphical display identifying the one or more recommended additional reports for the user.

2. The computer-implemented method of claim 1, further comprising:

querying a report database based at least in part on the report initiation data identifying one or more requested reports to determine standardized report data utilized to generate the one or more requested reports; and wherein generating the refined data table comprises generating table entries corresponding to the determined standardized report data utilized to generate the one or more requested reports within the refined data table.

3. The computer-implemented method of claim 1, wherein receiving raw health data from a plurality of health data storage systems further comprises standardizing the raw health data via Application Program Interfaces (APIs) executed by the corresponding data transmission interfaces.

4. The computer-implemented method of claim 1, wherein generating the one or more requested reports comprises:

determining an intended use for each of the one or more requested reports;

querying a formatting database based at least in part on the intended use determined for each of the one or more requested reports to determine formatting data relevant for each of the one or more requested reports; and generating the one or more requested reports based at least in part on formatting data relevant for each of the one or more requested reports.

5. The computer-implemented method of claim 1, wherein receiving raw health data from a plurality of health data storage systems further comprises:

scanning each of the one or more health data storage systems to determine data formats corresponding to raw health data received from each of the one or more health data storage systems; and assigning a data transmission interface to each of the one or more health data storage systems based at least in part on the data formats determined to correspond to raw data received from each of the one or more health data storage systems.

6. The computer-implemented method of claim 1, wherein generating a refined data table further comprises automatically assigning a standard procedure code for data entries within the standardized report data.

7. A computing system comprising a non-transitory computer readable storage medium and one or more processors, the computing system configured to:

receive report initiation data identifying one or more requested reports and identifying a user profile associated with the report initiation data;

receive via a plurality of data transmission interfaces, raw health data from a plurality of health data storage systems, wherein the raw health data from each of the plurality of health data storage systems is received through corresponding data transmission interfaces configured to standardize the raw health data;

apply a machine-learning quality control check to identify inaccurate data included within the raw health data;

upon identifying inaccurate data within the raw health data, remediate the inaccurate data within the raw health data;

after remediating the inaccurate data within the raw health data, generate a refined data table comprising standardized report data relevant for the one or more requested reports, wherein the standardized report data is generated from the raw health data received from the plurality of health data storage systems;

determine, via a machine-learning algorithm, one or more additional reports supported by the refined data table;

determine a relevance score for each of the one or more additional reports based at least in part on user attribute data reflected within user profile data associated with the identified user profile;

determine one or more recommended additional reports selected from the one or more additional reports based at least in part on the relevance score generated for each of the one or more additional reports;

generate the one or more requested reports based at least in part on the refined data table; and generate a graphical display identifying the one or more recommended additional reports for the user.

8. The computing system of claim 7, wherein the computing system is further configured to:

query a report database based at least in part on the report initiation data identifying one or more requested reports to determine standardized report data utilized to generate the one or more requested reports; and wherein generating the refined data table comprises generating table entries corresponding to the determined standardized report data utilized to generate the one or more requested reports within the refined data table.

9. The computing system of claim 7, wherein receiving raw health data from a plurality of health data storage systems further comprises standardizing the raw health data via Application Program Interfaces (APIs) executed by the corresponding data transmission interfaces.

10. The computing system of claim 7, wherein generating the one or more requested reports comprises:

determining an intended use for each of the one or more requested reports;

querying a formatting database based at least in part on the intended use determined for each of the one or more requested reports to determine formatting data relevant for each of the one or more requested reports; and generating the one or more requested reports based at least in part on formatting data relevant for each of the one or more requested reports.

11. The computing system of claim 7, wherein receiving raw health data from a plurality of health data storage systems further comprises:

scanning each of the one or more health data storage systems to determine data formats corresponding to raw health data received from each of the one or more health data storage systems; and assigning a data transmission interface to each of the one or more health data storage systems based at least in part on the data formats determined to correspond to raw data received from each of the one or more health data storage systems.

12. The computing system of claim 7, wherein generating a refined data table further comprises automatically assigning a standard procedure code for data entries within the standardized report data.

13. A computer program product comprising a non-transitory computer readable medium having computer program instructions stored therein, the computer program instructions when executed by a processor, cause the processor to:

receive report initiation data identifying one or more requested reports and identifying a user profile associated with the report initiation data;

receive via a plurality of data transmission interfaces, raw health data from a plurality of health data storage systems, wherein the raw EMR data from each of the plurality of health data storage systems is received through corresponding data transmission interfaces configured to standardize the raw health data;

apply a machine-learning quality control check to identify inaccurate data included within the raw health data;

upon identifying inaccurate data within the raw health data, remediate the inaccurate data within the raw health data;

after remediating the inaccurate data within the raw health data, generate a refined data table comprising standardized report data relevant for the one or more requested reports, wherein the standardized report data is generated from the raw health data received from the plurality of health data storage systems;

determine, via a machine-learning algorithm, one or more additional reports supported by the refined data table;

determine a relevance score for each of the one or more additional reports based at least in part on user attribute data reflected within user profile data associated with the identified user profile;

determine one or more recommended additional reports selected from the one or more additional reports based at least in part on the relevance score generated for each of the one or more additional reports;

generate the one or more requested reports based at least in part on the refined data table; and generate a graphical display identifying the one or more recommended additional reports for the user.

14. The computer program product of claim 13, wherein the computer program instructions are further configured to, when executed by a processor, cause the processor to:

query a report database based at least in part on the report initiation data identifying one or more requested reports to determine standardized report data utilized to generate the one or more requested reports; and wherein generating the refined data table comprises generating table entries corresponding to the determined standardized report data utilized to generate the one or more requested reports within the refined data table.

15. The computer program product of claim 13, wherein receiving raw health data from a plurality of health data storage systems further comprises standardizing the raw health data via Application Program Interfaces (APIs) executed by the corresponding data transmission interfaces.

16. The computer program product of claim 13, wherein generating the one or more requested reports comprises:

determining an intended use for each of the one or more requested reports;

querying a formatting database based at least in part on the intended use determined for each of the one or more requested reports to determine formatting data relevant for each of the one or more requested reports; and generating the one or more requested reports based at least in part on formatting data relevant for each of the one or more requested reports.

17. The computer program product of claim 13, wherein receiving raw health data from a plurality of health data storage systems further comprises:

scanning each of the one or more health data storage systems to determine data formats corresponding to raw health data received from each of the one or more health data storage systems; and assigning a data transmission interface to each of the one or more health data storage systems based at least in part on the data formats determined to correspond to raw data received from each of the one or more health data storage systems.

18. The computer program product of claim 13, wherein generating a refined data table further comprises automatically assigning a standard procedure code for data entries within the standardized report data.

* * * * *